(12) United States Patent
Corbea et al.

(10) Patent No.: US 9,359,680 B2
(45) Date of Patent: *Jun. 7, 2016

(54) RUTHENIUM OR OSMIUM COMPLEXES AND THEIR USES AS CATALYSTS FOR WATER OXIDATION

(71) Applicants: Javier Jesus Concepcion Corbea, Upton, NY (US); Zoufeng Chen, Chapel Hill, NC (US); Jonah Wesley Jurss, Berkeley, CA (US); Joseph L. Templeton, Chapel Hill, NC (US); Paul Hoertz, Morrisville, NC (US); Thomas J. Meyer, Chapel Hill, NC (US)

(72) Inventors: Javier Jesus Concepcion Corbea, Upton, NY (US); Zoufeng Chen, Chapel Hill, NC (US); Jonah Wesley Jurss, Berkeley, CA (US); Joseph L. Templeton, Chapel Hill, NC (US); Paul Hoertz, Morrisville, NC (US); Thomas J. Meyer, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/492,887

(22) Filed: Sep. 22, 2014

(65) Prior Publication Data
US 2015/0073143 A1 Mar. 12, 2015

Related U.S. Application Data

(63) Continuation of application No. 13/958,843, filed on Aug. 5, 2013, now Pat. No. 8,871,078, which is a continuation of application No. 12/862,538, filed on Aug. 24, 2010, now Pat. No. 8,524,903.

(60) Provisional application No. 61/236,219, filed on Aug. 24, 2009.

(51) Int. Cl.
C07F 15/00 (2006.01)
C25B 1/04 (2006.01)
C25B 9/00 (2006.01)
(Continued)

(52) U.S. Cl.
CPC . *C25B 9/00* (2013.01); *B01J 31/16* (2013.01); *B01J 31/183* (2013.01); *B01J 31/1815* (2013.01); *C07F 15/0053* (2013.01); *C25B 1/003* (2013.01); *C25B 1/04* (2013.01); *C25B 3/04* (2013.01); *C25B 11/04* (2013.01); *B01J 2231/70* (2013.01); *B01J 2531/0244* (2013.01); *B01J 2531/821* (2013.01); *B01J 2531/825* (2013.01); *Y02E 60/366* (2013.01); *Y02P 20/135* (2015.11)

(58) Field of Classification Search
CPC ......... C07F 15/0053; C25B 9/00; C25B 3/04; C25B 1/003; B01J 31/1815; B01J 31/183
USPC .............................................. 544/225; 546/2
See application file for complete search history.

(56) References Cited

U.S. PATENT DOCUMENTS
8,524,903 B2 9/2013 Corbea et al.
8,871,078 B2 10/2014 Corbea et al.

OTHER PUBLICATIONS
Chen et al., "Concerted O atom-proton transfer in the O—O bond forming step in water oxidation," Apr. 20, 2010, PNAS, vol. 107, No. 16, pp. 7225-7229.

(Continued)

*Primary Examiner* — Porfirio Nazario Gonzalez
(74) *Attorney, Agent, or Firm* — Thrive IP; Jeremy M. Stipkala

(57) ABSTRACT

The present invention provides ruthenium or osmium complexes and their uses as a catalyst for catalytic water oxidation. Another aspect of the invention provides an electrode and photo-electrochemical cells for electrolysis of water molecules.

7 Claims, 23 Drawing Sheets
(6 of 23 Drawing Sheet(s) Filed in Color)

(51) Int. Cl.
*B01J 31/16* (2006.01)
*B01J 31/18* (2006.01)
*C25B 1/00* (2006.01)
*C25B 11/04* (2006.01)
*C25B 3/04* (2006.01)

(56) References Cited

OTHER PUBLICATIONS

Chen et al., "Single-Site, Catalytic Water Oxidation on Oxide Surfaces," J. Am. Chem. Soc., JACS Communications, 2009, http://pubs.acs.org.

Concepcion et al., "Catalytic Water Oxidation by Single-Site Ruthenium Catalysts," Inorg. Chem., 2010, vol. 49, pp. 1277-1279.

Concepcion et al., "Mechanism of Water Oxidation by Single-Site Ruthenium Complex Catalysts," J. Am. Chem. Soc., 2010, vol. 132, pp. 1545-1557.

Mondal et al., "Example of Highly Stereoregulated Ruthenium Amidine Complex Formation: Synthesis, Crystal Structures, and Spectral and Redox Properties of the Complexes [RuII(trpy){NC5H4-CH=N-N(C6H5)C(CH3)=NH}] (ClO4)2 (1) and [RuII(trpy)(NC5H4-CH=N-NH-C6H5)Cl]ClO4 (2) (trpy = 2,2':6',2"-Terpyridine)," Inorg. Chem., 2002, vol. 41, No. 22, pp. 5831-5836.

Singh et al., "Ruthenium monoterpyridine complexes with 2,6-bis(benzoxazol-2-yl)pyridine as an ancillary ligand: Synthesis, structure and spectral studies," Polyhedron, 2008, vol. 27, pp. 2563-2568.

RUTHENIUM OR OSMIUM COMPLEXES AND THEIR USES AS CATALYSTS FOR WATER OXIDATION

RELATED APPLICATIONS

This application claims the benefit under 35 U.S.C. §120 and is a continuation of U.S. Non-Provisional patent application Ser. No. 13/958,843, filed on Aug. 5, 2013, now U.S. Pat. No. 8,871,078 B2, which claims the benefit under 35 U.S.C. §120 and is a continuation of U.S. Non-Provisional patent application Ser. No. 12/862,538, filed on Aug. 24, 2010, now U.S. Pat. No. 8,524,903 B2, which claims the benefit under 35 U.S.C. §119(e) of U.S. Provisional Patent Application Ser. No. 61/236,219, filed Aug. 24, 2009, the disclosures of which are incorporated herein by reference in their entirety.

GOVERNMENT SUPPORT

This invention was made, in-part, with United States government support under grants numbered DE-FG02-06ER15788 and DE-SC0001011 from the Department of Energy. The U.S. Government has certain rights to this invention.

FIELD OF THE INVENTION

The present invention generally relates to catalysts for water oxidation.

BACKGROUND OF THE INVENTION

Hydrogen is one of the most promising alternative energy sources. It can be obtained by electrolysis of water, which is environmentally friendly and efficient. However, the electrolysis of water is an energy intensive process, which is very expensive. On the other hand, photolysis, the splitting of water by light, presents an attractive alternative method of obtaining hydrogen. Additionally, light driven reduction of carbon dioxide by water to provide hydrocarbons or methanol may be another promising alternative to alternate energy sources. For both types of reactions, coupled water oxidation to oxygen is required. In order to facilitate the photolysis of water by light in either type of reaction, a catalyst is required for the reaction. However, there are very few catalysts found to be efficient and cost effective to carry out this reaction. (See, *Molecular, Catalysts for Water Oxidation*, Yagi et al, Chem. Rev., 101, 21-35 (2001)). For example, Gratzel et al., described that Ruthenium dimers can be used as catalysts for water oxidation. (See U.S. Pat. No. 5,223,634 to Gratzel et al.). More recently, Brimblecombe et al. have discovered that tetra-manganese-oxo cluster can also be used to catalyze water oxidation. (See PCT application WO 2008/116254 to Brimblecombe et al.). However, these catalysts are limited to the scope and ability to harness the photo chemical reactions.

Therefore, there is a need in the industry for an efficient catalyst for the electrolysis or photoelectrolysis of water to obtain hydrogen or water reduction of carbon dioxide to obtain affordable and sustainable alternative source of energy.

SUMMARY OF THE INVENTION

Some aspects of the present invention provide complexes comprising formula (I):

wherein M is ruthenium (Ru) or osmium (Os), $L_1$ is a bidentate ligand, $L_2$ is a tridentate ligand, $L_3$ is a monodentate ligand, and n is 2 or 1.

In one embodiment, $L_1$ is a bidentate ligand selected from

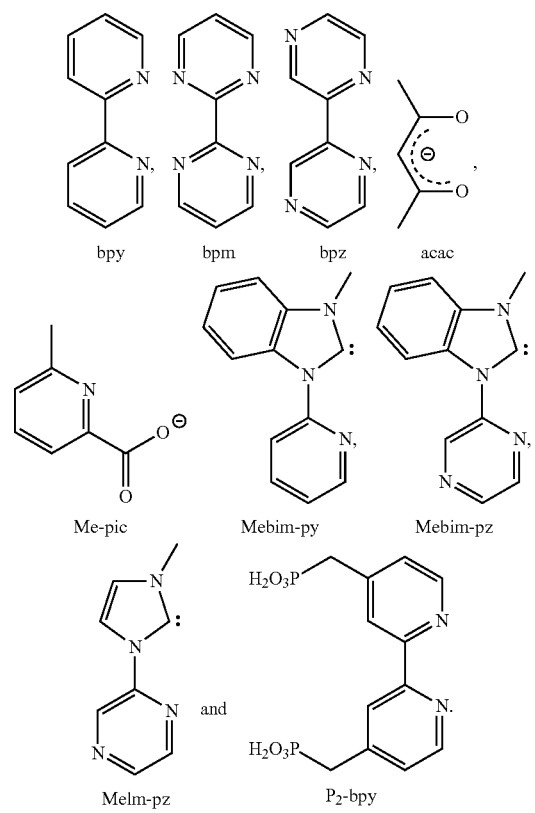

In another embodiment, $L_2$ is a tridentate ligand selected from

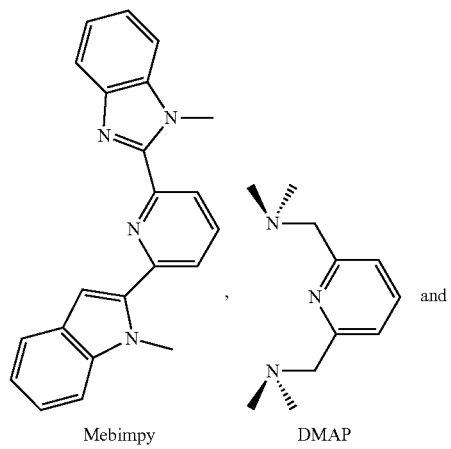

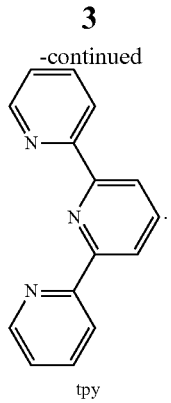

tpy

In one embodiment, $L_3$ is $OH_2$.

In some embodiment, the complex has a structure selected from the group consisting of $[Ru(tpy)(bpy)(OH_2)]^{2+}$, $[Ru(tpy)(bpm)(OH_2)]^{2+}$, $[Ru(tpy)(bpz)(OH_2)]^{2+}$, $[Ru(tpy)(Mcbim-pz)(OH_2)]^{2+}$, $[Ru(tpy)(Mebim-py)(OH_2)]^{2+}$, $[Ru(DMAP)(bpy)(OH_2)]^{2+}$, $[Ru(Mebimpy)(P_2-bpy)]^{2+}$, $[Ru(Mebimpy)(bpy)(OH_2)]^{2+}$, $[Ru(Mebimpy)(Mebim-pz)(OH_2)]^{2+}$, $[Ru(Mebimpy)(Mebim-py)(OH_2)]^{2+}$, $Ru(Mebimpy)(4,4'-CH_2PO_3H_2bpy)-(OH_2)^{2+}$, $\{Ru(Mebimpy)[4,4'-((HO)_2OPCH_2)_2bpy](OH_2)\}^{2+}$ and $OS(tpy)(bpy)(OH_2)^{2+}$.

According to another aspect of the invention, the complexes described above may be used as a catalyst for catalytic water oxidation.

A further aspect of the invention provides an electrode comprising a complex descried herein.

Another aspect of the present invention provides photoelectrochemical cells comprising a catalyst described herein.

Another aspect of the invention provides photoelectrolytic devices comprising a catalyst described herein and a supporting substrate on which said catalyst is supported.

A further aspect of the invention describes methods of generating hydrogen ($H_2$) and/or oxygen ($O_2$) gases. The method comprises providing a catalyst described herein and adding the catalyst to an electrolytic media under a condition effective to generate hydrogen and/or oxygen.

Another aspect of the invention describes methods of generating methanol, hydrocarbons and/or oxygen ($O_2$). The method comprises: providing a catalyst described herein and adding the catalyst to an electrolytic media under a condition effective to generate methanol, hydrocarbons and/or oxygen ($O_2$).

Objects of the present invention will be appreciated by those of ordinary skill in the art from a reading of the Figures and the detailed description of the preferred embodiments which follow, such description being merely illustrative of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The patent or application file contains at least one drawing executed in color. Copies of this patent or patent application publication with color drawings will be provided by the Office upon request and payment of the necessary fee.

DETAILED DESCRIPTION

Figure 1:
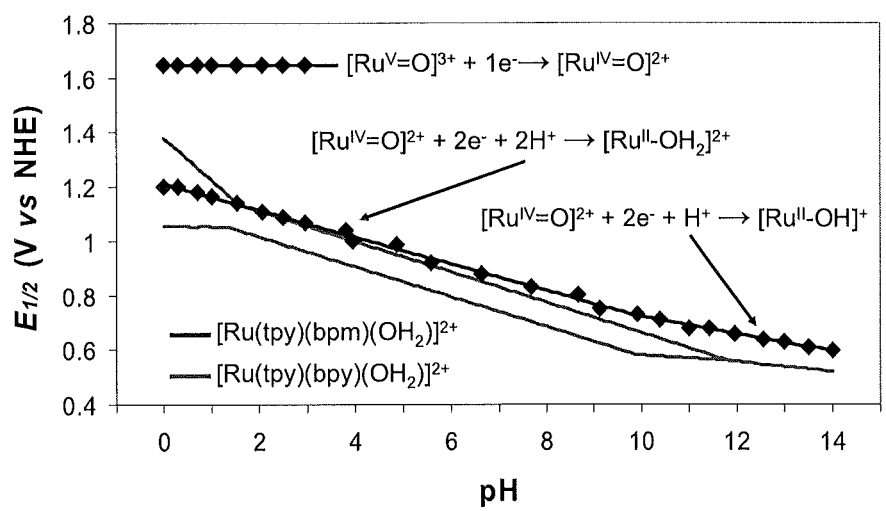
FIG. 1 demonstrates plots of $E_{1/2}$ (V vs NHE) vs pH for the Ru (V/IV) and Ru(IV/II) redox couples of $[Ru(tpy)(bpm)(OH_2)]^{2+}$ and for the Ru(IV/III) and Ru(III/II) redox couples of $[Ru(tpy)(bpy)(OH_2)]^{2+}$ in aqueous solution (I=0.1 M; T=298 K; glassy carbon working electrode).
Figure 2:
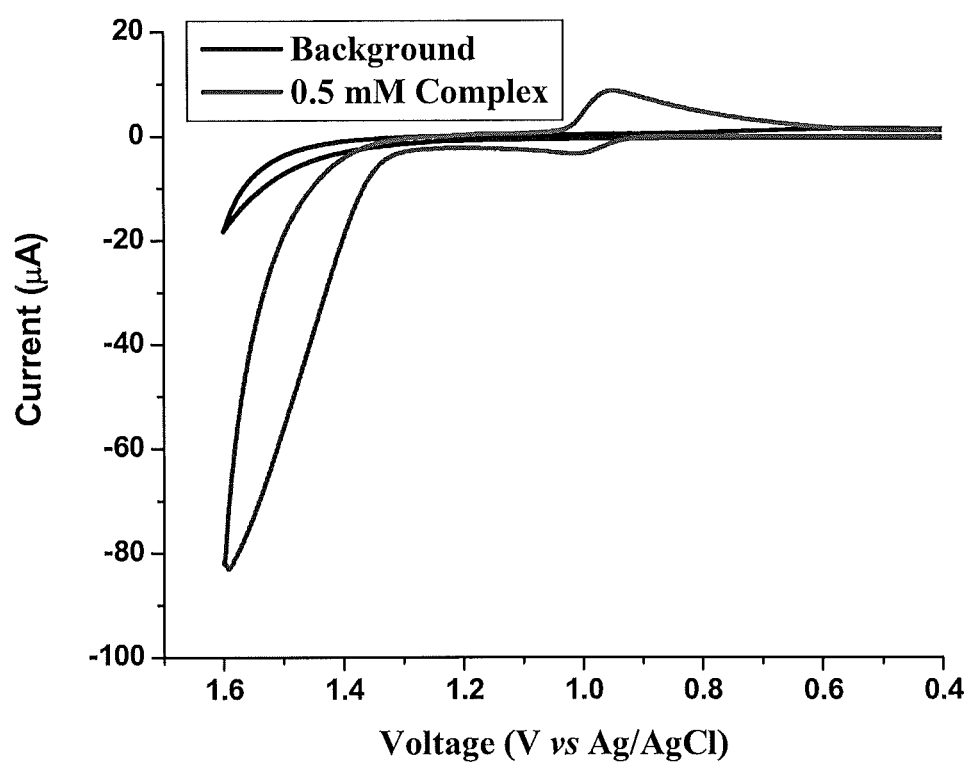
FIG. 2 demonstrates plots of current versus voltage in solution of Ag/AgCl for background and 0.5 mM $[Ru(tpy)(bmp)(OH_2)]^{2+}$.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In case of a conflict in terminology, the present specification is controlling.

A. Complexes

Provided herein according to some embodiments of the invention are complexes, which comprise the structure of formula (I):

wherein M is ruthenium (Ru) or osmium (Os), and $L_1$, $L_2$ and $L_3$ may be any combinations of any ligands as long as the combination meets the bonding requirement for M. n+ represents the positive charge for the complex of formula I. The value of n depends on the specific combination of M and ligands of $L_1$, $L_2$ and $L_3$. In some embodiments, n is 2 or 1. Any applicable anions may be used to bond with the complex of formula I. the In some embodiments, $L_1$ may be any applicable bidentate ligand that is known to one skilled in the art, $L_2$ may be any applicable tridentate ligand that is known to one skilled in the art and $L_3$ may be any applicable monodentate ligand that is known to one skilled in the art. In one embodiment, $L_3$ is $OH_2$. According to the investigators of the present application, the considerations of selecting the ligands include, but are not limited to, the following: (1) the stability toward oxidation by the high oxidation state oxo forms of the catalysts; (2) the ability electronically to provide the metal (e.g. Ru or Os) to access higher oxidation state IV and V oxidation states by oxo formation; and (3) the resulting potential for multi-electron oxidation of water being sufficient to be thermodynamically allowed.

As used herein, a ligand is either an atom, ion, or molecule that binds to a central metal to produce a coordination complex. The bonding between the metal and ligand generally involves formal donation of one or more of the ligand's electrons. The monodentate ligand is a ligand with one lone pair of electrons that is capable of binding to an atom (e.g. a metal atom). Exemplary monodentate ligands include, but are not limited to, $OH_2$ (aqua), $NH_3$ (ammine), $CH_3NH_2$ (methylamine), CO (carbonyl), NO (nitrosyl), $F^-$ (fluoro), $CN^-$ (cyano), $Cl^-$ (chloro), $Br^-$ (bromo), $I^-$ (iodo), $NO_2^-$ (nitro), and $OH^-$ (hydroxyl). In some embodiments, the monodentate ligand is $H_2O$. The bidentate ligand is a ligand with two lone pairs of electron that are capable of binding to an atom (e.g. a metal atom). Exemplary bidentate ligands include, but are not limited to, bipyridine, phenanthroline, 2-phenylpyridine bipyrimidine, bipyrazyl, glycinate, acetylacetonate, 2,6-bis (1-methylbenzimidazol-2-yl)pyridine (mebim-py) and ethylenediamine. The tridentate ligand and terdentate ligand is a ligand with respectively three or four lone pairs of electron that are capable of binding to an atom (e.g. a metal atom). Exemplary tridentate ligands include, but are not limited to, terpyridine, DMAP, and Mebimpy.

The terminology of monodentate ligand, bidentate ligand, and tridentate ligand are well known to those skilled in the art. Further exemplary monodentate ligand, bidentate ligand, and tridentate ligand are described in U.S. Pat. Nos. 7,488,817, 7,368,597, 7,291,575, 7,232,616, 6,946,420, 6,900,153, 6,734,131, 4,481,184, 4,019,857, and 4,452,774, which are incorporated by references in their entirety.

The bidentate ligands and tridentate ligands used in the present invention may be optionally substituted with one or more substituents. Any applicable substituents may be used. Exemplary substituents include, but are not limited to, carboxylic acid, ester, amide, halogen, anhydride, acyl ketone, alkyl ketone, acid chloride, sulfonic acid, phosphonic acid, nitro and nitroso groups. The substituents may be located at any acceptable location on the ligand and may include any number of substituents which may be substituted on the particular ligand.

More exemplary $L_1$ include, but are not limited to,

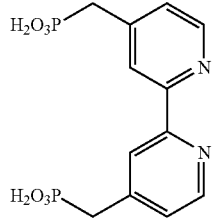

2,2'-bipyridine (bpy), 2,2'-bipyrimidine (bpm), 2,2'-bipyrimidine (bpm),

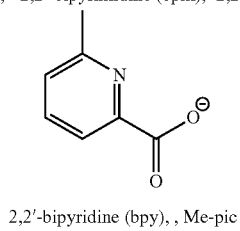

2,2'-bipyridine (bpy), , Me-pic

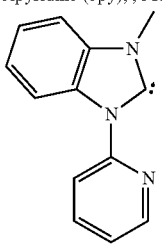

2,6-bis(1-methylbenzimidazol-2-yl)pyridine (Mebim-py),

-continued

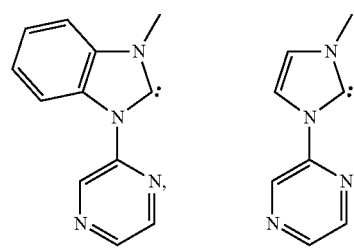

Mebim-pz        Melm-pz

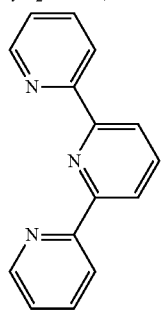

$P_2$-bpy        , and    acetylacetonate (acac).

More exemplary $L_2$ include, but are not limited to,

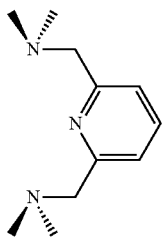

2,2':6',2''-terpyridine (tpy),

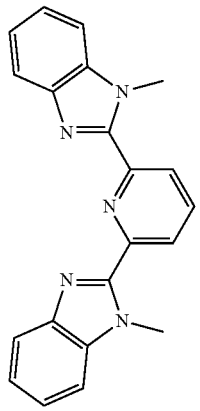

2,6-bis( (dimethylamino)methyl)pyridine (DMAP), and 2,6-bis(1-methylbenzimidazol-2-yl)pyridine (Mebimpy).

The complex provided according to some embodiments of the invention is selected from:
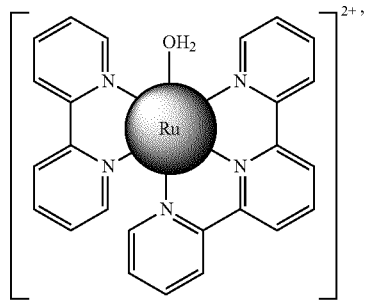
[Ru(tpy)(bpy)(OH$_2$)]$^{2+}$,
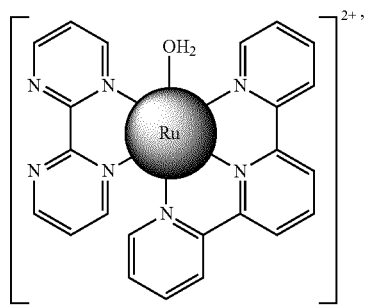
[Ru(tpy)(bpm)(OH$_2$)]$^{2+}$,
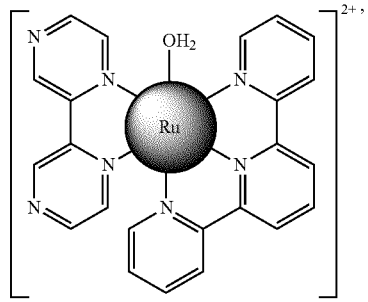
[Ru(tpy)(bpz)(OH$_2$)]$^{2+}$,
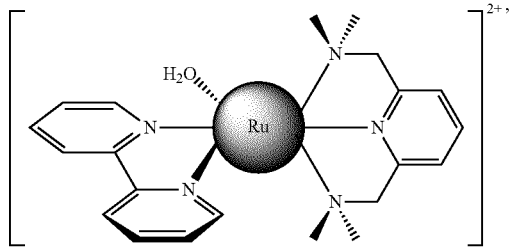
[Ru(DMAP)(bpy)(OH$_2$)]$^{2+}$,
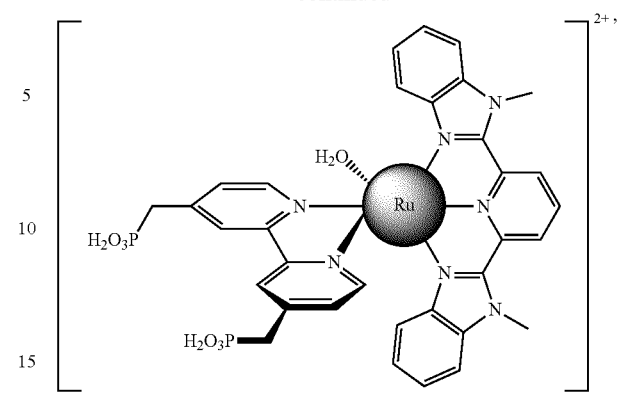
[Ru(Mebimpy)(P$_2$-bpy)]$^{2+}$,
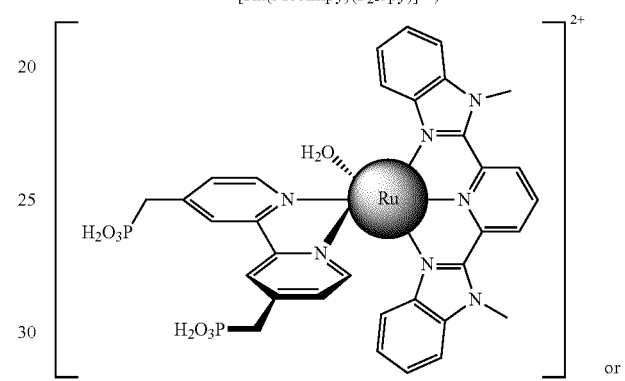
{Ru(Mebimpy)[4,4'-((HO)$_2$OPCH$_2$)$_2$bpy](OH$_2$)}$^{2+}$ (1-PO$_3$H$_2$),
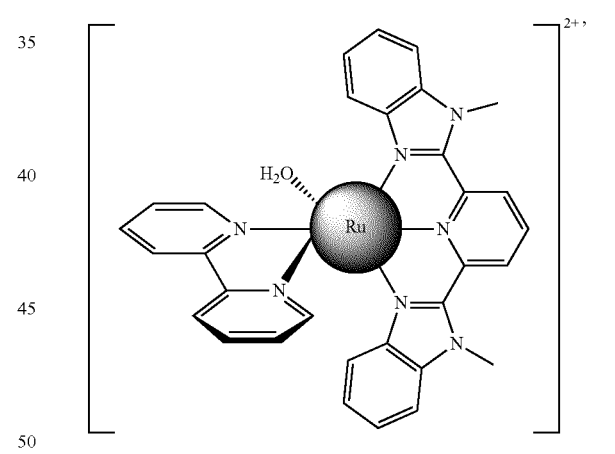
[Ru(Mebimpy)(bpy)OH$_2$)]$^{2+}$
Formula A
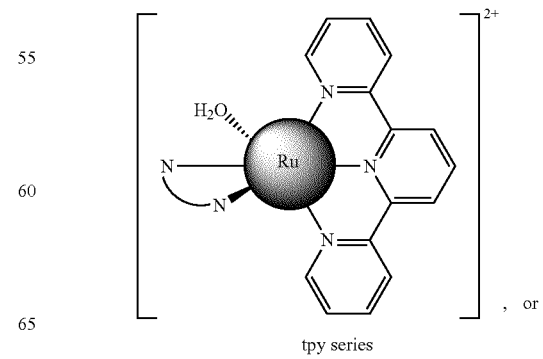
tpy series
, or -continued Formula B

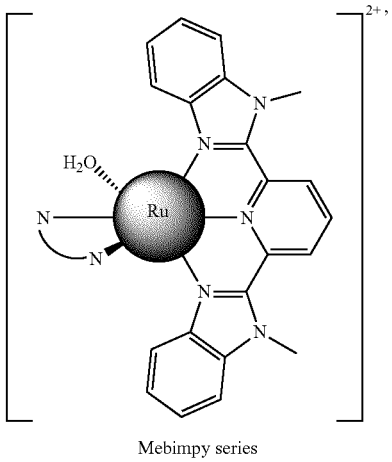

Mebimpy series wherein: for formula A and B

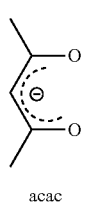 is independently selected from

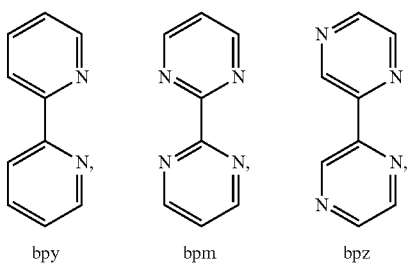

bpy     bpm     bpz

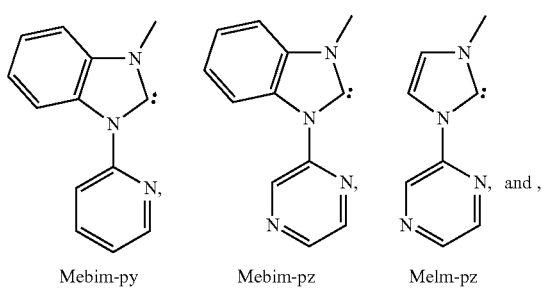

Mebim-py     Mebim-pz     MeIm-pz acac

In some embodiments, for Formula A and B,

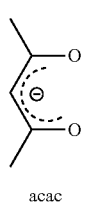 is independently selected from the group consisting of

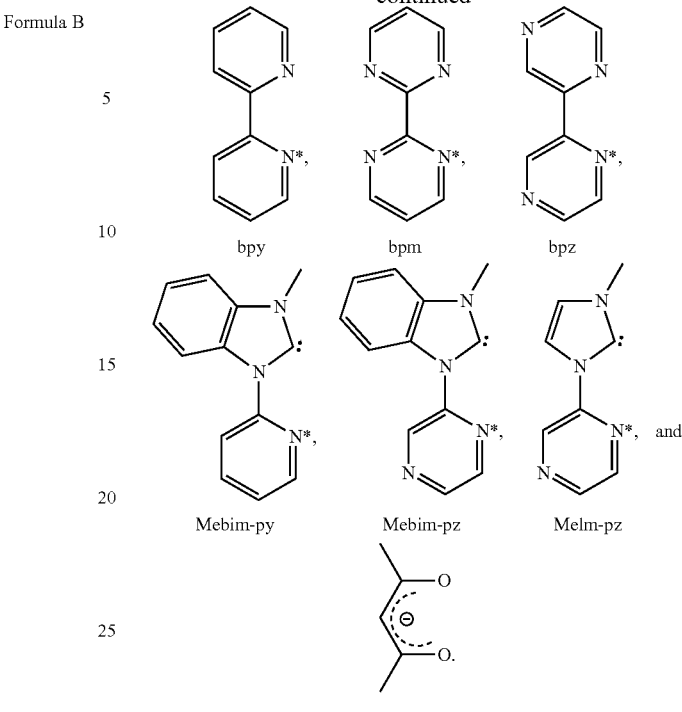

bpy     bpm     bpz

Mebim-py     Mebim-pz     MeIm-pz, and acac wherein Ruthenium bonds to the N* or an electron lone pair or the electron delocalized oxygen of the ligand.

In one embodiment, the complex is a structure selected from the group consisting of [Ru (tpy)(bpy)(OH$_2$)]$^{2+}$, [Ru (tpy)(bpm)(OH$_2$)]$^{2+}$, [Ru(tpy)(bpz)(OH$_2$)]$^{2+}$, [Ru(tpy)(Mebim-pz)(OH$_2$)]$^{2+}$, [Ru(tpy)(Mebim-py)(OH$_2$)]$^{2+}$, [Ru (DMAP)(bpy)(OH$_2$)]$^{2+}$, [Ru(Mebimpy)(P$_2$-bpy)]$^{2+}$, [Ru (Mebimpy)(bpy)(OH$_2$)]$^{2+}$, [Ru(Mebimpy)(Mebim-pz) (OH$_2$)]$^{2+}$, [Ru(Mebimpy)(Mebim-py)(OH$_2$)]$^{2+}$, Ru(Mebimpy)(4,4'-CH$_2$PO$_3$H$_2$bpy)-(OH$_2$)$^{2+}$, {Ru(Mebimpy)[4,4'-((HO)$_2$OPCH$_2$)$_2$bpy](OH$_2$)}$^{2+}$ and Os(tpy)(bpy)(OH$_2$)$^{2+}$.

B. Synthesis

Compounds described herein may be prepared by using methods described in the literature with modifications known to one skilled in the art.

For example, [Ru(tpy)(LL)(OH$_2$)]$^{n+}$ complexes with LL=bpy, bpm, bpz and acac may be prepared according to methods known to one skilled in the art. (See Concepcion, et al., *J Am. Chem. Soc.* 2008, 130(49), 16462-16463, Dovletoglou, et al., *Inorg. Chem.* 1996, 35(14), 4120-4127, Takeuchi, et al., *Inorg. Chem.* 1984, 23(13), 1845-1851, and Takeuchi, et al., *Inorg. Chem.* 1984, 23(13), 1845-1851.)

The synthesis of the [Ru(Mebimpy)(LL)(OH$_2$)]$^{n+}$ complexes with LL=bpy, bpm, bpz and acac may be accomplished following procedures similar to those used for the corresponding tpy complexes discussed above. They may involve isolation of the [Ru(Mebimpy)(NN)(Cl)]$^{n+}$ complexes followed by replacement of the chloro ligand in water assisted by added silver triflate or triflic acid. The trans-[Ru(tpy)(NC) (OH$_2$)]$^{2+}$, trans-[Ru(Mebimpy)(NC)(OH$_2$)]$^{2+}$ complexes and trans-[Ru(DMAP)(NC)(OH$_2$)]$^{2+}$ (NC is 3-methyl-1-pyridylimidazol-2-ylidene, MeIm-py; 3-methyl-1-pyridylbenzimidazol-2-ylidene, Mebim-py; and 3-methyl-1-pyrazylbenzimidazol-2-ylidene, Mebim-pz) may be obtained by reaction of the monocalionic carbene precursors with Ru(tpy) Cl$_3$, Ru(Mebimpy)Cl$_3$ or Ru(DMAP)Cl$_3$ in ethyleneglycol at 150° C. in the presence of NEt$_3$. (See Sullivan et al., *Inorg. Chem.* 1980, 19(5), 1404-1407, Welch, et al., *Inorg. Chem.* 1997, 36(21), 4812-4821.) In these cases the aquo complexes are isolated rather than chloro complexes most likely due to a trans-labilizing effect of the carbene on chloride ligand loss, since only the trans isomer is obtained, see below. For example, [Ru(Mebimpy)(4,4'-((OH)$_2$OPCH$_2$)$_2$-bpy)(OH$_2$)]$^{2+}$ may be prepared by a modification of the procedure used to synthesize [Ru(Mebimpy)(bpy)(OH$_2$)]$^{2+}$ with an extra step required to hydrolyze the phosphonate ester groups. Ru(DMAP)(bpy)(OH$_2$)$^{2+}$ may be prepared following a literature procedure. All complexes may be characterized by $^1$H-NMR, elemental analysis, absorption spectroscopy and cyclic voltammetry. More exemplary syntheses of some compounds described herein are discussed in Examples sections.

C. Catalyst, Electrode, and Cell for Electrocatalytic Reaction

According to some embodiments, the compounds described herein may be used as a catalyst. In some embodiments, the catalyst described herein may be used for electrocatalytic reaction (e.g. electrocatalytic water oxidation).

Figure 4:
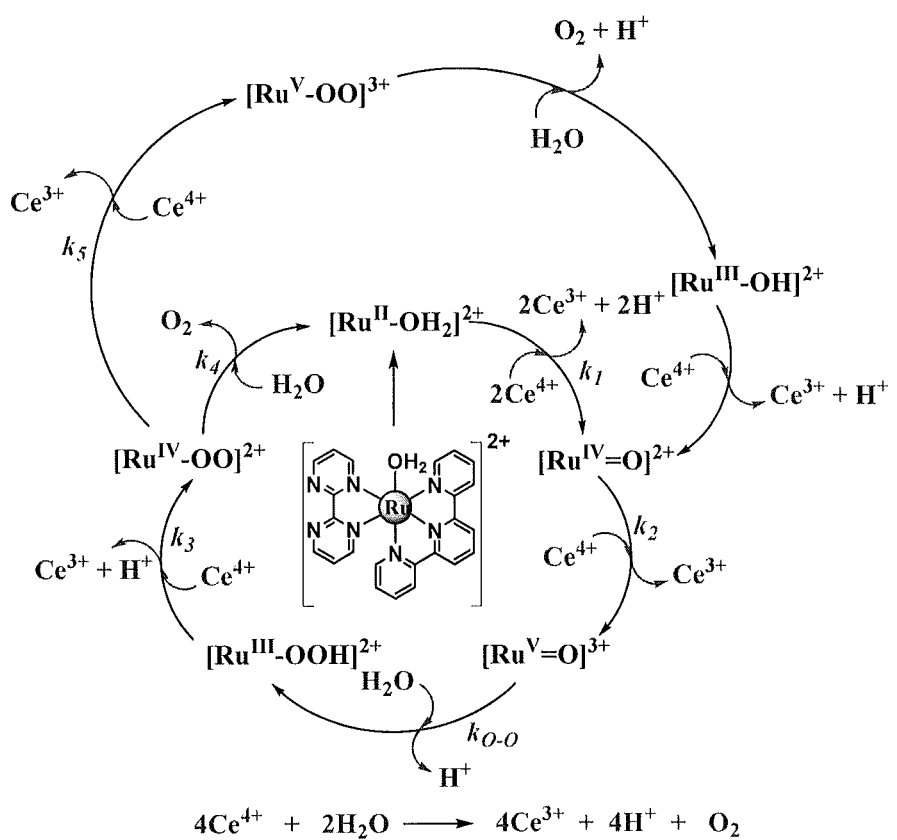
FIG. 4 demonstrates proposed mechanism for water oxidation by single-site catalysts $[Ru(tpy)(bpm)(OH_2)]^{2+}$ and $[Ru(tpy)(bpz)(OH_2)]^{2+}$ in 0.1 M $HNO_3$.

As a non-limiting example, the proposed mechanism of the electrolysis of water catalyzed by some exemplary compound of the present invention is proposed in FIG. 4. The compounds disclosed herein can be used as a catalyst for electrochemical, chemical and/or photochemical water oxidation.

According to some observations of the investigators, for most single site Ru complexes, it appears to be a common mechanism utilizing PCET oxidation to Ru$^{IV}$=O$^{n+}$ followed by further oxidation and water attack on Ru$^V$=O$^{(n+)+}$ to give Ru$^{III}$-OOH$^{n+}$. The O—O bond forming reaction is reminiscent of well documented O-atom transfer to sulfides, sulfoxides, phosphines, and olefins by Ru(bpy)$_2$(py)(O)$^{2+}$ and Ru(tpy)(bpy)(O)$^{2+}$. (See Meyer, et al., *Inorg. Chem.* 2003, 42(25), 8140-8160.) Furthermore, it appears that water oxidation catalysis appears to be general for polypyridyl aqua complexes with coordinated H$_2$O which have oxidatively stable ligands, the ability to reach higher oxidation state Ru=O intermediates, and the driving force to carry out water oxidation.

In addition, the investigators of the present invention have observed that the compounds described herein are effective for catalytic (e.g. Ce (IV)) water oxidation undergoing hundreds of turnovers without decomposition of the catalyst.

Furthermore, it is also observed that the ligand electronic effects on reactivity may affect the rates and overvoltage's for catalytic water oxidation. (See Example 5 and FIG. 6)

Another aspect of the present invention provides an electrode. In some embodiments, the electrode may be used for the electrolysis of water molecules comprising a catalyst comprising a compound described herein on the electrode substrate. As used herein, "electrode" is an electrical conductor used to make contact with a nonmetallic part of a circuit (e.g. a semiconductor, an electrolyte or a vacuum).

In some embodiments, the electrode may be an anode. For example, the catalysts described herein are added to the surfaces of anodes where oxidation occurs by application of an electrical potential or on photoanodes where the required potential is created by light absorption and electron transfer. In some embodiments, the electrode further comprises a supporting substrate. Any applicable supporting substrate may be used in the present invention. In some embodiments, the supporting substrate comprising fluorine-doped SnO$_2$ (FTO) or Sn(IV)-doped In$_2$O$_3$ (ITO). It is observed by the investigators of the present application that the surface bound complex of the catalyst comprising compounds described herein retains its chemical (E$_{1/2}$ values, pH dependence) and physical properties (UV-visible spectra) including its ability to catalyze water oxidation. In some embodiments, electrocatalysis reaction catalyzed by catalyst described herein may occur on TiO$_2$ which has been used in dye-sensitized solar cells.

The electrode may be prepared according to any applicable methods known to one skilled in the art. For example, U.S. Pat. No. 4,797,182 to Beer et al., U.S. Pat. No. 4,402,996 to Gauger et al., U.S. Pat. No. 7,320,842 to Ozaki et al., and U.S. 20090169974 to Tabata, which are incorporated by references in their entireties.

A further aspect of the present invention provides a photo-electrochemical cell comprising a complex described herein. In some embodiments, the photo-electrochemical cell is referred to as solar cells which generate electrical energy from light, including visible light. In some embodiments, the visible light is used for chemical conversion reactions at a separate electrode. In one aspect, the cell may be used for electrolysis of water oxidation. In one embodiment, the cell further comprises a base. In one embodiment, the bases include at least one proton acceptor base. As used herein, a proton acceptor base is any substance that is capable of accepting a proton. Exemplary proton acceptor base includes, but are not limited to, H$_2$PO$_4^-$ acetate (OAc$^-$), and HPO$_4^{2-}$. The investigators of the present application have observed that the addition of bases such as proton acceptor bases may enhance the rate of the electro catalytic water oxidation. It is believed that the addition of the bases accelerates the O—O bond formation of Ru$^{III}$-OOH$^{2+}$ by concerted atom-proton transfer (APT) with the added base acting as a proton acceptor decreasing the barrier in the key O—O bond forming step. The photo-electrochemical cell may be prepared according to any applicable methods known to one skilled in the art, for example, U.S. Pat. No. 4,388,384 to Rauh et al., U.S. Pat. No. 4,793,910 to Smotkin et al., U.S. Pat. No. 5,525,440 to Kay et al., and U.S. Pat. No. 6,376,765 to Wariishi et al., which are incorporated by references in their entireties.

A further aspect of the present invention provides a photo-electrolytic device comprising a catalyst, wherein the catalyst comprises a complex described herein, and a supporting substrate on which said catalyst is supported. In one embodiment, the device further comprises a base. In one embodiment, the bases include at least one proton acceptor base described above. The device may be prepared according to any applicable methods known to one skilled in the art. For example, U.S. Pat. No. 4,756,807 to Meyer, US 2007/0137998 to Sykora et al., and U.S. 20090169974 to Tabata, which are incorporated by references in their entireties.

A further aspect of the present invention provides methods of generating hydrogen (H$_2$) and/or oxygen (O$_2$) gases. In one embodiment, the method comprises providing a catalyst described herein, and adding the catalyst to an electrolytic media under a condition effective to generate hydrogen and/or oxygen. In one embodiment, the methods further comprise exposing the reaction media, which contains the catalyst to light radiation to generate hydrogen and/or oxygen gases.

In another embodiment, the method comprises exposing the photo-electrochemical cell described herein to light radiation to generate hydrogen and oxygen gases without the requirement of applying an external electrical potential. In one embodiment, the method further comprises adding at least one proton acceptor base described above.

Another aspect of the present invention provides methods of generating hydrocarbons, methanol and/or oxygen (O$_2$) gases by photo-electrolyzing water. The method comprises providing a catalyst described herein and adding the catalyst to a electrolytic media under an effective condition to generate methanol/hydrocarbons and/or oxygen (O$_2$). In one embodiment, the method further comprises exposing the reaction media which contain the catalyst to light radiation to generate methanol, hydrocarbons and/or oxygen ($O_2$). In another embodiment, the method comprises exposing the photo-electrochemical cell described herein to light radiation without the requirement of applying an external electrical potential. In one embodiment, the method further comprises adding at least one proton acceptor base described above.

The present invention will now be described in more detail with reference to the following examples. However, these examples are given for the purpose of illustration and are not to be construed as limiting the scope of the invention.

EXAMPLES

Materials and Methods

Distilled water was further purified using a Milli-Q Ultrapure water purification system. Stock solutions of $Ce^{IV}$ for kinetic and stoichiometric measurements were prepared from $(NH_4)_2Ce(NO_3)_6$ (99.99+%, Aldrich). Nitric acid (Trace Metal Grade, 70%) was purchased from Fisher Scientific and perchloric acid (70%, purified by redistillation, 99.999% trace metals basis) was purchased from Aldrich. 2,2'-bipyrimidine (97%) and $RuCl_3 \times 3H_2O$ were purchased from Aldrich and used as received. 2,2'-bipyrazine[1] and $[Ru(tpy)Cl_3]^2$ were prepared as described in the literature. [Ru(tpy)(bpm)$(OH_2)](PF_6)_2$ and $[Ru(tpy)(bpz)(OH_2)](PF_6)_2$ (bpm is 2,2'-bipyrimidine and bpz is 2,2'-bipyrazine) were prepared according to methods described in Concepcion, J. J.; Jurss, J. W.; Templeton, J. L.; Meyer, T. J. *J. Am. Chem. Soc.* 2008, 130(49), 16462-16463. All other reagents were ACS grade and used without additional purification. 2,6-Bis(1-methyl-benzimidazol-2-yl)pyridine (Mebimpy) was prepared as reported for 2,6-bis(benzimidazol-2-yl)pyridine. See Xu, X.; Xi, Z.; Chen, W.; Wang, D. *J. Coord. Chem.* 2007, 60, 2297-2308. [Ru(Mebimpy)(N—N)(Cl)](Cl) (N—N) bpy or bpm) was prepared by a modification of the procedure reported for [Ru-(tpy)(bpm)(Cl)](PF6). See Swavey, S.; Fang, Z.; Brewer, K. J. *Inorg. Chem.* 2002, 41, 2598-2607.

Elemental analyses were conducted by Atlantic Microlab, Inc., Atlanta, Ga. UV/Vis spectra and UV/Vis spectra vs time were recorded on an Agilent Technologies Model 8453 diode-array spectrophotometer. Kinetic measurements were also performed on a Shimadzu UV-Vis-NIR Spectrophotometer Model UV-3600 by monitoring the disappearance of $Ce^{IV}$ at 360 nm Electrochemical measurements were performed on an EG&G Princeton Applied Research model 273A potentiostat/galvanostat. Voltammetric measurements were made with a planar EG&G PARC G0229 glassy carbon millielectrode, a platinum wire EG&G PARC K0266 counter electrode, and Ag/AgCl EG&G PARC K0265 reference electrode.

Oxygen Evolution Experiments

Oxygen measurements were performed with a calibrated $O_2$ electrode (YSI, Inc., Model 550A) or with a fluorescence-based YSI ProODO $O_2$ calibrated electrode. In a typical experiment, 30 equivalents of $Ce^{IV}$ were added to stirred solutions containing $1.0-2.9 \times 10^{-3}$ M ruthenium complex in 1.0 or 0.1 M $HNO_3$. The air-tight reaction cell was purged with argon prior to the addition of the $Ce^{IV}$ until the digital readout had stabilized. $O_2$ evolution vs time was recorded and the theoretical maximum was achieved ±3%.

Synthesis and Characterization

Ligands

2,6-bis(1-methylbenzimidazol-2-yl)pyridine (Mebimpy)

This ligand was prepared by a modification of the procedure reported for 2,6-bis(benzimidazol-2-yl)pyridine.[4] A mixture of pyridine-2,6-dicarboxylic acid (3.35 g, 20 mmol) and N-methyl-1,2-phenylenediamine (5.38 g, 44 mmol) in 40 mL of 85% phosphoric acid was stirred at ca 230° C. for 4 h. The dark green melt was poured into 1 L of vigorously stirred cold water. After it was cooled to room temperature, the blue precipitate was collected by filtration, then slurried into 300 mL of hot aqueous sodium carbonate solution (10%). The resulting solid was filtered off and recrystallized from methanol to give a white solid. Yield: 5.77 g, 85%. $^1$H NMR ($CDCl_3$): δ 8.42 (d, 2H), 8.05 (t, 1H), 7.86-7.89 (m, 2H), 7.44-7.48 (m, 2H), 7.33-7.41 (m, 4H), 4.25 (s, 6H, 2$CH_3$). This ligand was pure by $^1$H-NMR and was used without further purification.

2,6-bis(dimethylaminomethyl)pyridine (DMAP)

This ligand was prepared according to a methods described in Hull, J. F.; Balcells, D.; Blakemore, J. D.; Incarvito, C. D.; Eisenstein, O.; Brudvig, G. W.; Crabtree, R. H. *J. Am. Chem. Soc.* 2009, 131(25), 8730-8731.

N-Methyl-N'-2-pyridylimidazolium hexafluorophosphate (MeIm-py$^+$PF6$^-$)

This ligand was synthesized by a modification of a literature procedure.[6] A mixture of 2-bromopyridine (3.16 g, 20.0 mmol) and 1-methylimidazole (1.64 g, 20.0 mmol) was kept neat at 160° C. for 48 h. After cooling to ca 50° C., acetone was added and the resulting solid was filtered and washed with acetone and ether. The solid was dissolved in water, filtered and added to aqueous ammonium hexafluorophosphate. Upon standing for 2 hours the solid was isolated by filtration and washed with water and ether. Yield: 4.27 g (70%). $^1$H NMR ($CD_3CN$): δ 9.25 (s, 1H, NCHN), 8.59 (d, 1H), 8.08-8.12 (dt, 1H), 8.06 (t, 1H), 7.72 (d, 1H), 7.56-7.59 (dd, 1H), 7.54 (t, 1H), 3.96 (s, 3H, $CH_3$). This ligand was pure based on $^1$H-NMR and was used without further purification.

N-Methyl-N'-2-pyridylbenzimidazolium iodide (Mebim-py$^+$I$^-$)

A mixture of 2-iodopyridine (2.0 g, 9.8 mmol) and 1-methylbenzimidazole (1.29 g, 9.8 mmol) was kept neat at 140° C. for 72 h. After cooling to ca 50° C., acetone was added and the resulting solid was filtered and washed with acetone and ether. Yield: 826 mg (25%). $^1$H NMR (DMSO-d$_6$): δ 10.48 (s, 1H, NCHN), 8.79 (d, 1H), 8.47-8.49 (m, 1H), 8.27-8.32 (dt, 1H), 8.14-8.16 (m, 1H), 8.04 (d, 1H), 7.77-7.82 (m, 2H), 7.71-7.74 (dd, 1H), 4.20 (s, 3H, $CH_3$). This ligand was pure by $^1$H-NMR and was used without further purification.

N-Methyl-N'-2-pyrazylbenzimidazolium iodide (Mebim-pz$^+$I$^-$)

A mixture of 2-iodopyrazine (2.0 g, 9.7 mmol) and 1-methylbenzimidazole (1.28 g, 9.7 mmol) was kept neat at 135° C. for 72 h. After cooling to ca 50° C., acetone was added and the resulting solid was filtered and washed with acetone and ether. Yield: 1.1 g (34%). $^1$H NMR (DMSO-d$_6$): δ 10.59 (s, 1H, NCHN), 9.36 (s, 1H, pz), 8.97 (d, 1H), 8.88-8.90 (m, 1H), 8.47-8.49 (m, 1H), 8.17-8.19 (m, 1H), 7.79-7.85 (m, 2H), 4.23 (s, 3H, CH$_3$). This ligand was pure by $^1$H-NMR and was used without further purification.

4,4'-Bis(diethylmethylphosphonate)-2,2'-bipyridine (4,4'-(H$_2$O$_3$PCH$_2$)$_2$-bpy)

This ligand was prepared by the procedure described in Welch et al., *Inorg. Chem*, 1997, 36(21), 4812-4821.

Complexes

Ru(tpy)Cl$_3$

This complex was synthesized according to methods described in Huynh, M. H. V.; Meyer, T. J., *Chem. Rev.*, 2007, 107(11), 5004-5064.

Ru(Mebimpy)Cl$_3$

This complex was synthesized as reported for Ru(tpy)Cl$_3$[2] using Mebimpy instead of tpy. In a typical experiment RuCl$_3$×3H$_2$O (1.00 g, 3.83 mmol) and Mebimpy (1.30 g, 3.83 mmol) were mixed in 400 mL of ethanol and the mixture refluxed for 3 hours. Upon cooling to room temperature, the brown solid was filtered, washed with ethanol until the ethanol came out clear and finally with ether. Yield: 1.6 g, 76%. This compound was used without further purification.

Ru(DMAP)Cl$_3$

This complex was synthesized by a modification of a literature procedure.[5] RuCl$_3$×3H$_2$O (2.0 g, 7.66 mmol) and DMAP (1.48 g, 7.66 mmol) were refluxed in ethanol (50 mL) for 3 hours. Upon cooling the green solid was filtered and washed with ethanol and ether. This solid was refluxed in 30 mL of concentrated HCl for ~30 min to yield the product as an orange powder that was collected by filtration and washed with water and ether. This compound was used without further purification.

((Mebimpy)(Cl)Ru)$_2$Cl$_2$

Ru(Mebimpy)Cl$_3$ (500 mg,) was suspended in ethanol (40 mL) and the mixture degassed by bubbling argon trough it. Triethylamine (1.5 mL) was added and the mixture refluxed for 2 hours and filtered hot. The purple solid obtained was washed with ethanol and ether to remove [Ru(Mebimpy)$_2$]Cl$_2$, which is soluble in ethanol. This impurity is the result of reduction of [Ru(Mebimpy)$_2$]Cl$_3$ that forms as a byproduct in the synthesis of Ru(Mebimpy)Cl$_3$. [((Mebimpy)(Cl)Ru)$_2$Cl$_2$] was used without further purification.

Ru(tpy)(bpy)(OH$_2$)(ClO$_4$)$_2$

This complex was prepared according to methods described in Takeuchi, K. J.; Thompson, M. S.; Pipes, D. W.; Meyer, T. J., *Inorg., Chem.* 1984, 23(13), 1845-1851.

Ru(tpy)(Mebim-py)(OH$_2$)(ClO$_4$)$_2$.2H$_2$O

Ru(tpy)Cl$_3$ (500 mg, 1.13 mmol) and Mebim-py$^+$I$^-$ (382 mg, 1.13 mmol) were suspended in ethyleneglycol and degassed by bubbling argon. Triethylamine (1.0 mL) was added with a syringe and the mixture was heated at 150° C. for 3 hours. The crude product was isolated by addition of aqueous ammonium hexafluorophosphate and washed with water and ether. The brown solid obtained was dissolved in acetone and aqueous potassium nitrate was added. The solvents were removed by rotary evaporation and a small amount of 0.1 M HNO$_3$ was added. The mixture was filtered to remove undissolved materials and the filtrate was loaded on a column (Sephadex LH-20) and eluted with 0.1 M HNO$_3$. The yellow-orange band was collected and added to saturated aqueous sodium perchlorate. Upon standing in the refrigerator overnight crystals of Ru(tpy)(Mebim-py)(OH$_2$)(ClO$_4$)$_2$.2H$_2$O formed. The product was isolated by filtration, washed with ice-cold water and air-dried. Yield: 315 mg, 35%. Anal. Found (Calc.) for C$_{28}$H$_{28}$Cl$_2$N$_6$O$_{11}$Ru: C, 42.25 (42.22); N, 10.68 (10.55); H, 3.45 (3.54). $^1$H NMR (CD$_3$CN, as Ru(tpy)(Mebim-py)(CD$_3$CN)$^{2+}$): δ 9.44 (d, 1H), 8.52 (d, 3H), 8.40 (d, 2H), 8.35-8.39 (dt, 1H), 8.27-8.31 (t, 1H), 8.16 (d, 1H), 7.99-8.03 (dt, 2H), 7.73-7.76 (m, 1H), 7.59 (d, 2H), 7.41-7.45 (dt, 1H), 7.35-7.39 (dt, 1H), 7.30-7.34 (m, 2H), 7.27 (d, 1H), 2.90 (s, 3H, CH$_3$).

Ru(tpy)(Mebim-pz)(OH$_2$)(NO$_3$)(PF$_6$).2H$_2$O

Ru(tpy)Cl$_3$ (500 mg, 1.13 mmol) and Mebim-pz$^+$I$^-$ (382 mg, 1.13 mmol) were suspended in ethyleneglycol and degassed by bubbling argon. Triethylamine (1.0 mL) was added with a syringe and the mixture was heated at 150° C. for 2 hours. The crude product was isolated by addition of aqueous ammonium hexafluorophosphate and washed with water and ether. The brown solid obtained was dissolved in acetone and aqueous potassium nitrate was added. The mixture was filtered to remove undissolved materials and the filtrate was allowed to stand for several days. The dark red crystals of Ru(tpy)(Mebim-pz)(OH$_2$)(NO$_3$)(PF$_6$).2H$_2$O were isolated by filtration, washed with ice-cold water, ether and air-dried. Yield: 450 mg, 49%. Anal. Found (Calc.) for C$_{27}$H$_{27}$F$_6$N$_8$O$_6$PRu: C, 40.81 (40.25); N, 13.58 (13.91); H, 3.28 (3.38). $^1$H NMR (CD$_3$CN, as Ru(tpy)(Mebim-pz)(CD$_3$CN)$^{2+}$): δ 10.2 (d, 1H), 9.72 (s, 1H, pz) 8.80 (d, 1H), 8.49 (d, 2H), 8.6 (d, 2H), 8.19-8.23 (t, 2H), 7.90-7.94 (t, 2H), 7.54 (d, 2H), 7.34-7.43 (m, 2H), 7.21-7.24 (dd, 3H), 2.96 (s, 3H, CH$_3$).

Ru(tpy)(MeIm-py)(OH$_2$)(ClO$_4$)$_2$

Ru(tpy)Cl$_3$ (500 mg, 1.13 mmol) and MeIm-py$^+$PF$_6^-$ (345 mg, 1.13 mmol) were suspended in ethyleneglycol and degassed by bubbling argon. Triethylamine (1.0 mL) was added with a syringe and the mixture was heated at 150° C. for 2 hours. Aqueous sodium perchlorate was added and the mixture was filtered. The filtrate was allowed to stand for several hours and a black microcrystalline solid formed. It was isolated by filtration, washed with ice-cold water and air-dried. Yield: 520 mg, 65%. Anal Found (Calc.) for C$_{24}$H$_{22}$Cl$_2$N$_6$O$_9$Ru: C, 40.50 (40.57); N, 11.72 (11.83); H, 3.12 (3.13). $^1$H NMR (CD$_3$CN, as Ru(tpy)(MeIm-py)(CD$_3$CN)$^{2+}$): δ 9.36 (d, 1H), 8.49 (d, 2H) 8.39 (d, 2H), 8.26-8.30 (t, 1H), 8.21-8.25 (t, 1H), 8.00-8.06 (m, 3H), 7.90 (d, 1H), 7.70-7.74 (t, 1H), 7.60 (d, 2H), 7.34-7.37 (t, 2H), 6.85 (d, 1H), 2.71 (s, 3H, CH$_3$).

Ru(tpy)(acac)(OH$_2$)(PF$_6$)

This complex was prepared as reported in Adeyemi, S. A.; Dovletoglou, A.; Guadalupe, A. R.; Meyer, T. J., *Inorg. Chem.*, 1992, 31(8), 1375-1383.

[Ru(Mebimpy)(bpy)(Cl)](Cl)

[((Mebimpy)(Cl)Ru)$_2$Cl$_2$] (300 mg, 0.29 mmol) and bpy (92 mg, 59 mmol) were suspended in 45 mL of 2:1 EtOH:H$_2$O and the mixture was degassed by argon bubbling. The suspension was heated at reflux for 4 hours and 10 mL of 20% aqueous LiCl were added. After an additional 20 min the mixture was filtered hot and the filtrate was allowed to cool overnight. The brown microcrystalline solid formed was isolated by filtration and washed with water and ether. Yield: 329 mg, 85%. $^1$H-NMR (CD$_3$OD): δ 10.68 (d, 1H), 8.83 (d, 1H), 8.71 (d, 2H), 8.44-8.48 (td, 1H), 8.36 (d, 1H), 8.20-8.24 (t, 1H), 8.09-8.12 (td, 1H), 7.69 (d, 2H), 7.56-7.60 (td, 1H), 7.46 (d, 1H), 7.38-7.42 (t, 2H), 4.51 (s, 6H, 2CH$_3$). This compound was used without further purification.

[Ru(Mebimpy)(bpy)(OTf)](OTf).4H$_2$O (OTf is the triflate anion). A mixture of [Ru(Mebimpy)(bpy)(Cl)](Cl) (267 mg, 0.40 mmol) and AgOTf (218 mg, 0.85 mmol) in MeOH (20 mL) were stirred under argon at room temperature overnight. The silver chloride was removed by filtration using a bed of Celite and the filtrate was taken to dryness by rotary evaporation. Diethyl ether was added and the solid was filtered, washed with ether and air dried. Yield: 348 mg, 90%. Anal. Found (Calc.) for C$_{33}$H$_{33}$F$_6$N$_7$O$_{10}$RuS$_2$: C, 41.09 (40.99); N, 10.13 (10.14); H, 2.86 (3.44). $^1$H-NMR (CD$_3$CN, 400 MHz, as [Ru(Mebimpy)(bpy)(CD$_3$CN)](OTf)$_2$) δ 10.10 (d, 1H), 8.70 (d, 1H), 8.67 (d, 2H), 8.49 (td, 1H), 8.36 (t, 1H), 8.28 (d, 1H), 8.07-8.10 (m, 1H), 7.72 (td, 2H), 7.69 (d, 2H), 7.44-7.48 (m, 2H), 7.41 (d, 1H), 7.13-7.17 (m, 2H), 7.07-7.10 (m, 1H), 6.20 (d, 2H), 4.44 (s, 6H, 2CH$_3$).

[Ru(Mebimpy)(bpy)(OH$_2$)](OTf)$_2$

This complex was prepared in-situ dissolving [Ru(Mebimpy)(bpy)(OTf)](OTf) in water. UV-Vis (0.1 M HNO$_3$) λ$_{max}$, nm (ε, M$^{-1}$cm$^{-1}$): 487 (12600), 358 (40460), 343 (34700), 315 (27150), 290 (46300), 253 (sh, 32000), 245 (34700). UV-Vis (0.01 M NaOH) λ$_{max}$, nm (ε, M$^{-1}$cm$^{-1}$): 600 (sh, 3970), 518 (11620), 357 (39500), 342 (33050), 315 (24450), 292 (50500), 255 (sh, 26650), 241 (31770).

[Ru(Mebimpy)(bpm)(Cl)](Cl)

[Ru(Mebimpy)Cl$_3$] (700 mg, 1.28 mmol) and bpm (203 mg, 1.28 mmol) were suspended in 60 mL of 2:1 EtOH:H$_2$O and the mixture was degassed by argon bubbling. Triethylamine (2.5 mL) was added with a syringe and the suspension was heated at reflux for 4 hours. 20 mL of 20% aqueous LiCl were added and the brown microcrystalline solid formed was isolated by filtration and washed with water and ether. Yield: 728 mg, 85%. $^1$H-NMR (CD$_3$CN): δ 10.89-10.91 (dd, 1H), 9.42-9.44 (dd, 1H), 8.58 (d, 3H), 8.13-8.18 (m, 2H), 7.70-7.72 (dd, 1H), 7.63 (d, 2H), 7.39-7.44 (td, 2H), 7.09-7.13 (t, 2H), 6.99-7.02 (t, 1H), 6.24 (d, 2H), 4.40 (s, 6H, 2CH$_3$). This compound was used without further purification.

[Ru(Mebimpy)(bpm)(OTf)](OTf).5H$_2$O (OTf is the triflate anion). A mixture of [Ru(Mebimpy)(bpm)(Cl)](Cl) (268 mg, 0.40 mmol) and AgOTf (218 mg, 0.85 mmol) in MeOH (20 mL) were stirred under argon at room temperature overnight. The silver chloride was removed by filtration using a bed of Celite and the filtrate was taken to dryness by rotary evaporation. Diethyl ether was added and the solid was filtered, washed with ether and air dried. Yield: 359 mg, 91%. Anal Found (Calc.) for C$_{31}$H$_{23}$F$_6$N$_9$O$_6$RuS$_2$.5H$_2$O: C, 37.63 (37.73); N, 12.59 (12.77); H, 2.77 (3.37). $^1$H-NMR (D$_2$O, 400 MHz, as [Ru(Mebimpy)(bpy)(D$_2$O)](OTf)$_2$), δ 10.27 (dd, 1H); 9.42 (d, 1H); 8.64 (d, 2H); 8.45 (dd, 1H); 8.26 (t, 2H); 8.24 (d, 1H); 7.74 (dd, 1H); 7.61 (d, 2H); 7.37 (t, 2H); 7.06 (t, 2H); 6.99 (t, 1H); 6.23 (d, 2H); 4.40 (s, 6H, 2CH$_3$).

[Ru(Mebimpy)(bpm)(OH$_2$)](OTf)$_2$

This complex was prepared in-situ dissolving [Ru(Mebimpy)(bpm)(OTf)](OTf) in water. UV-Vis (0.1 M HNO$_3$) λ$_{max}$, nm (ε, M$^{-1}$ cm$^{-1}$): 526 (sh, 4120), 439 (9070), 359 (34180), 345 (28140), 316 (21700), 245 (37640). UV-Vis (0.01 M NaOH) λ$_{max}$, nm (ε, M$^{-1}$cm$^{-1}$): 572 (sh, 4840), 494 (8360), 358 (31400), 344 (25950), 315 (20350), 302 (18300), 262 (sh, 29650), 245 (33600).

[Ru(Mebimpy)(bpz)(Cl)](Cl)

[Ru(Mebimpy)Cl$_3$] (700 mg, 1.28 mmol) and bpz (203 mg, 1.28 mmol) were suspended in 25 mL of 4:1 ethyleneglycol:H$_2$O and the mixture was degassed by argon bubbling. Triethylamine (2.5 mL) was added with a syringe and the suspension was heated at 140° C. for 3 hours. 20 mL of 20% aqueous LiCl were added and the black microcrystalline solid formed was isolated by filtration and washed with water and ether. Yield: 745 mg, 87%. $^1$H-NMR (DMSO-d$_6$): δ 10.62 (d, 1H), 10.23 (s, 1H), 9.75 (s, 1H), 9.27 (d, 1H), 8.81 (d, 2H), 8.35-8.39 (t, 1H), 8.17 (d, 1H), 7.87 (d, 2H), 7.76 (d, 1H), 7.38-7.42 (t, 2H), 7.11-7.15 (t, 2H), 6.04 (d, 2H), 4.50 (s, 6H, 2CH$_3$). This compound was used without further purification.

[Ru(Mebimpy)(bpz)(OTf)](OTf).4H$_2$O (OTf is the triflate anion). A mixture of [Ru(Mebimpy)(bpz)(Cl)](Cl) (268 mg, 0.40 mmol) and AgOTf (218 mg, 0.85 mmol) in MeOH (20 mL) were stirred under argon at room temperature overnight. The silver chloride was removed by filtration using a bed of Celite and the filtrate was taken to dryness by rotary evaporation. Diethyl ether was added and the solid was filtered, washed with ether and air dried. Yield: 359 mg, 91%. Anal. Found (Calc.) for C$_{31}$H$_{31}$F$_6$N$_9$O$_{10}$RuS$_2$: C, 38.13 (38.43); N, 13.26 (13.01); H, 2.97 (3.23). $^1$H-NMR (CD$_3$CN, 400 MHz, as [Ru(Mebimpy)(bpz)(CD$_3$CN)](OTf)$_2$) δ 10.20 (d, 1H), 9.90 (s, 1H), 9.47 (s, 1H), 9.18 (d, 1H), 8.70 (d, 2H), 8.43-8.47 (t, 1H), 8.21 (d, 1H), 7.68 (d, 2H), 7.59 (d, 1H), 7.43-7.47 (t, 2H), 7.14-7.18 (t, 2H), 6.18 (d, 2H), 4.42 (s, 6H, 2CH$_3$).

[Ru(Mebimpy)(bpz)(OH$_2$)](OTf)$_2$

This complex was prepared in-situ dissolving [Ru(Mebimpy)(bpz)(OTf)](OTf) in water. UV-Vis (0.1 M HNO$_3$) λ$_{max}$, nm (ε, M$^{-1}$cm$^{-1}$): 509 (6760), 428 (6450), 357 (27230), 343 (sh, 22880), 308 (32550).

Ru(Mebimpy)(Mebim-py)(OH$_2$)(OTF)$_2$.H$_2$O

Ru(Mebimpy)Cl$_3$ (618 mg, 1.13 mmol) and Mebim-py$^+$I$^-$ (382 mg, 1.13 mmol) were suspended in ethyleneglycol and degassed by bubbling argon. Triethylamine (1.0 mL) was added with a syringe and the mixture was heated at 150° C. for 3 hours. The crude product was isolated by addition of aqueous lithium triflate and washed with water and ether. The brown solid obtained was dissolved in 1:1 MeOH:H$_2$O, filtered to remove undissolved materials and the filtrate was loaded on a column (Sephadex LH-20) and eluted with 1:1 MeOH:H$_2$O. The yellow-orange band was collected and added to saturated aqueous lithium triflate. Upon standing in the refrigerator overnight Ru(Mebimpy)(Mebim-py)(OH$_2$)(OTf)$_2$.H$_2$O formed. The product was isolated by filtration, washed with ice-cold water and air-dried. Yield: 450 mg, 40%. Anal. Found (Calc.) for C$_{36}$H$_{32}$F$_6$N$_8$O$_8$RuS$_2$: C, 43.79 (43.95); N, 11.32 (11.39); H, 3.14 (3.28). $^1$H NMR (CD$_3$CN, as Ru(Mebimpy)(Mebim-py)(CD$_3$CN)$^{2+}$): δ 9.83-9.85 (dd, 1H), 8.58-8.62 (t, 3H), 8.49-8.53 (dt, 1H), 8.30-8.34 (t, 1H), 8.12 (d, 1H), 7.81-7.84 (dt, 1H), 7.67 (d, 2H), 7.40-7.43 (t, 2H), 7.33-7.37 (dt, 1H), 7.28-7.32 (t, 1H), 7.20 (d, 1H), 7.08-7.12 (t, 2H), 6.09 (d, 2H), 4.39 (s, 6H, 2CH$_3$, Mebimpy), 2.99 (s, 3H, CH$_3$, Mebim-py).

Ru(Mebimpy)(MeIm-py)(OH$_2$)(OTf)$_2$.2H$_2$O

Ru(Mebimpy)Cl$_3$ (618 mg, 1.13 mmol) and MeIm-py$^4$PF$_6^-$ (345 mg, 1.13 mmol) were suspended in ethyleneglycol and degassed by bubbling argon. Triethylamine (1.0 mL) was added with a syringe and the mixture was heated at 150° C. for 3 hours. The crude product was isolated by addition of aqueous lithium triflate and washed with water and ether. The brown solid obtained was dissolved in 1:1 MeOH:H$_2$O, filtered to remove undissolved materials and the filtrate was loaded on a column (Sephadex LH-20) and eluted with 1:1 MeOH:H$_2$O. The yellow-orange band was collected and added to saturated aqueous lithium triflate. Upon standing in the refrigerator overnight Ru(Mebimpy)(MeIm-py)(OH$_2$)(OTf)$_2$.2H$_2$O formed. The product was isolated by filtration, washed with ice-cold water and air-dried. Yield: 484 mg, 45%. Anal. Found (Calc.) for C$_{36}$H$_{32}$F$_6$N$_8$O$_8$RuS$_2$: C, 40.36 (40.38); N, 11.74 (11.77); H, 3.25 (3.39). $^1$H NMR (CD$_3$CN, as Ru(Mebimpy)(MeIm-py)(CD$_3$CN)$^{2+}$): δ 9.77 (d, 1H), 8.58 (d, 2H), 8.39-8.43 (t, 1H), 8.24-8.28 (t, 1H), 8.10 (d, 1H), 7.84 (d, 1H), 7.78-7.82 (t, 1H), 7.69 (d, 2H), 7.43-7.47 (t, 2H), 7.11-7.15 (t, 2H), 6.77 (d, 1H), 6.10 (d, 2H), 4.40 (s, 6H, 2CH$_3$, Mebimpy), 2.80 (s, 3H, CH$_3$, MeIm-py).

Ru(Mebimpy)(acac)(OH$_2$)(OTf).H$_2$O

Neat triflic acid (2.0 mL) was added to 300 mg (0.29 mmol) of [((Mebimpy)(Cl)Ru)$_2$Cl$_2$] and the mixture was stirred for 1 hour. Addition of ether causes precipitation of a red solid which was filtered and washed with ether. This solid is presumably Ru(Mebimpy)(OTf)$_3$ and was used in the next step without further characterization. The obtained Ru(Mebimpy)(OTf)$_3$, acetylacetone (71 mg, 0.645 mmol) and methanol (40 mL) were degassed by argon bubbling and triethylamine (2.0 mL) was added with a syringe. The mixture was heated at reflux for 3 hours and water was added, followed by 10% aqueous lithium triflate. The purple solid was filtered and washed with water and ether and dried under vacuum. Yield: 400 mg, 94%. Anal. Found (Calc.) for C$_{36}$H$_{32}$F$_6$N$_8$O$_8$RuS$_2$: C, 44.89 (44.75); N, 9.69 (9.66); H, 3.87 (3.89).

Ru(Mebimpy)(4,4'-(H$_2$O$_3$PCH$_2$)$_2$-bpy)(OH$_2$)(OTf)$_2$

Ru(Mebimpy)Cl$_3$ (618 mg, 1.13 mmol), 4,4'-((OEt)$_2$OPCH$_2$)$_2$-bpy (516 mg, 1.13 mmol) and LiCl (100 mg) were suspended in 45 mL of 2:1 EtOH:H$_2$O and degassed by bubbling argon. Triethylamine (1.0 mL) was added with a syringe and the mixture was heated at reflux for 5 hours. 10% aqueous lithium chloride (20 mL) was added and the precipitate of Ru(Mebimpy)(4,4'-(OEt)$_2$OPCH$_2$)$_2$-bpy)(Cl)(Cl) was isolated by filtration and washed with water and ether. This solid was refluxed in 60 mL of 4.0 M aqueous HCl for 5 days to hydrolyze the phosphonate ester groups. After cooling to room temperature, the purple precipitate of Ru(Mebimpy)(4,4'-(H$_2$O$_3$PCH$_2$)$_2$-bpy)(Cl)(Cl) was isolated by filtration and washed with water and ether. To this solid, triflic acid (3.0 mL) was added, and the mixture was stirred at room temperature for 2 hours. Hydroquinone (124 mg, 1.13 mmol) dissolved in 10 mL of water was added to reduce any Ru(III) species and after a few minutes aqueous lithium triflate was added to complete precipitation of the product. The maroon solid was isolated by filtration, washed with water, ether and air-dried. Yield: 896 mg, 72%. Anal. Found (Calc.) for C$_{35}$H$_{33}$F$_6$N$_7$O$_{13}$P$_2$RuS$_2$: C, 38.73 (38.19); N, 9.19 (8.91); H, 3.95 (3.02). $^1$H NMR (CD$_3$OD): δ 9.83-9.91 (dd, 1H), 8.81 (d, 2H), 8.77 (d, 2H), 8.33-8.37 (t, 1H), 8.28-8.32 (t, 1H), 8.12-8.18 (dd, 1H), 7.70-7.74 (t, 2H), 7.42 (d, 1H), 7.39 (d, 1H), 7.11-7.20 (m, 2H), 6.92 (d, 1H), 6.31-6.35 (t, 2H), 4.56 (s, 6H, 2CH$_3$, Mebimpy), 3.66 (d, 2H, CH$_2$), 2.97 (d, 2H, CH$_2$).

Ru(DMAP)(bpy)(OH$_2$)(PF$_6$)$_2$.1.5H$_2$O

This complex was prepared by a modification of a literature procedure for Ru(DMAP)(bpy)(OH$_2$)(ClO$_4$)$_2$.2H$_2$O, which was described in Hull et al., *J. Am. Chem. Soc.*, 2009, 131 (25), 8730-8731. Ru(DMAP)Cl$_3$ (500 mg, 1.25 mmol), bpy (195 mg, 1.25 mmol) and zinc powder (1.00 g) were suspended in water (60 mL) and degassed by bubbling argon. The mixture was heated at reflux for 1 hour and filtered hot through a bed of Celite. The crude product was isolated by addition of aqueous ammonium hexafluorophosphate and washed with water and ether. The red solid obtained was dissolved in MeOH, filtered to remove undissolved materials and added to aqueous ammonium hexafluorophosphate. The MeOH was removed by rotary evaporation and the dark red needles of Ru(DMAP)(bpy)(OH$_2$)(PF$_6$)$_2$.1.5H$_2$O formed were filtered and washed with cold water and ether. Yield: 589 mg, 60%. Anal. Found (Calc.) for C$_{21}$H$_{32}$F$_{12}$N$_5$O$_{2.5}$P$_2$Ru: C, 32.10 (32.11); N, 8.90 (8.92); H, 4.03 (4.11). $^1$H NMR (CD$_3$CN, as Ru(DMAP)(bpy)(CD$_3$CN)$^{2+}$): δ 9.49 (d, 1H), 8.55 (d, 1H), 8.51 (d, 1H), 8.10-8.14 (dt, 1H), 8.05-8.09 (dt, 1H), 7.98-8.02 (t, 1H), 7.93 (d, 1H), 7.75-7.78 (dt, 1H), 7.64 (d, 2H), 7.47-7.51 (dt, 1H), 4.11 (d, 2H, H CH$_2$(1), H CH$_2$(2)), 3.92 (d, 2H, H CH$_2$(2), H CH$_2$(1)), 2.36 (s, 6H, 3H CH$_3$(1), 3H CH$_3$(2)), 1.49 (s, 6H, 3H CH$_3$(2), 3H CH$_3$(1)).

Ru(DMAP)(MeIm-py)(OH$_2$)(PF$_6$)$_2$.0.5H$_2$O

Ru(DMAP)Cl$_3$ (250 mg, 0.63 mmol) and MeIm-py$^+$PF6$^-$ (191 mg, 0.63 mmol) were suspended in ethyleneglycol and degassed by bubbling argon. Triethylamine (1.0 mL) was added with a syringe and the mixture was heated at 150° C. for 3 hours. The product was isolated by addition of aqueous ammonium hexafluorophosphate and washed with water and ether and air-dried. Yield: 290 mg, 60%. Anal. Found (Calc.) for C$_{20}$H$_{31}$F$_{12}$N$_6$O$_{1.5}$P$_2$Ru: C, 31.11 (31.18); N, 12.02 (10.91); H, 4.02 (4.06). $^1$H NMR (CD$_3$CN, as Ru(DMAP)(MeIm-py)(CD$_3$CN)$^{2+}$): δ 9.29 (d, 2H), 8.01 (d, 1H), 7.96 (d, 1H), 7.79-7.82 (t, 1H), 7.50-7.53 (t, 1H), 7.44 (d, 2H), 6.48 (s, 1H), 3.95 (d, 2H, H CH$_2$(1), H CH$_2$(2)), 3.89 (d, 2H, H CH$_2$(2), H CH$_2$(1)), 3.81 (s, 3H, CH$_3$, MeIm-py), 2.26 (s, 6H, 3H CH$_3$(1), 3H CH$_3$(2)), 1.67 (s, 6H, 3H CH$_3$(2), 3H CH$_3$(1)).

Ru(DMAP)(Mebim-py)(OH$_2$)(PF$_6$)$_2$.2H$_2$O

Ru(DMAP)Cl$_3$ (250 mg, 0.63 mmol) and Mebim-py$^+$I$^-$ (212 mg, 0.63 mmol) were suspended in ethyleneglycol and degassed by bubbling argon. Triethylamine (1.0 mL) was added with a syringe and the mixture was heated at 150° C. for 3 hours. The product was isolated by addition of aqueous ammonium hexafluorophosphate and washed with water and ether and air-dried. Yield: 281 mg, 55%. Anal. Found (Calc.) for $C_{24}H_{36}F_{12}N_6O_3P_2Ru$: C, 33.92 (34.01); N, 9.83 (9.92); H, 4.19 (4.28). $^1H$ NMR ($CD_3CN$, as Ru(DMAP)(MeIm-py) $(CD_3CN)^{2+}$): δ 9.29 (d, 1H), 8.46 (d, 1H), 8.23-8.26 (m, 1H), 8.15-8.20 (dt, 1H), 7.97-8.00 (t, 1H), 7.62 (d, 2H), 7.50-7.58 (m, 4H), 4.22 (d, 2H, H $CH_2(1)$, H $CH_2(2)$), 3.93 (d, 2H, H $CH_2(2)$, H $CH_2(1)$), 334 (s, 3H, $CH_3$, Mebim-py), 2.36 (s, 6H, 3H $CH_3(1)$, 3H $CH_3(2)$), 1.77 (s, 6H, 3H $CH_3(2)$, 3H $CH_3(1)$).

[Ru(Mebimpy)(N—N)(OTf)](OTf)

A mixture of [Ru(Mebimpy)-(N—N)(Cl)](Cl) (0.50 mmol) and AgOTf (1.05 mmol; OTf) triflate anion) in MeOH (40 mL) was stirred under argon at room temperature overnight. The silver chloride was removed by filtration using a bed of Celite, and the filtrate was taken to dryness by rotary evaporation. Diethyl ether was added, and the solid was filtered, washed with ether, and air-dried.

[Ru(Mebimpy)(bpy)(OTf)](OTf)

1H NMR ($CD_3CN$, 400 MHz, as [Ru(Mebimpy)(bpy) $(CD_3CN)](OTf)_2$): δ 10.10 (d, 1H), 8.70 (d, 1H), 8.67 (d, 2H), 8.49 (td, 1H), 8.36 (t, 1H), 8.28 (d, 1H), 8.07-8.10 (m, 1H), 7.72 (td, 2H), 7.69 (d, 2H), 7.44-7.48 (m, 2H), 7.41 (d, 1H), 7.13-7.17 (m, 2H), 7.07-7.10 (m, 1H), 6.20 (d, 2H), 4.44 (s, 6H, 2CH3). Anal. Found (calcd) for $C_{33}H_{25}F_6N_7O_6RuS_2 \cdot 4H_2O$: C, 41.09 (40.99); N, 10.13 (10.14); H, 2.86 (3.44). High-resolution MS (ESI, m/z): 746.0735 (M+).

[Ru(Mebimpy)(bpm)(OTf)](OTf)

1H NMR ($D_2O$, 400 MHz, as [Ru(Mebimpy)(bpy)(D2O)] $(OTf)_2$): δ 10.27 (dd, 1H), 9.42 (d, 1H), 8.64 (d, 2H), 8.45 (dd, 1H), 8.26 (t, 2H), 8.24 (d, 1H), 7.74 (dd, 1H), 7.61 (d, 2H), 7.37 (t, 2H), 7.06 (t, 2H), 6.99 (t, 1H), 6.23 (d, 2H), 4.40 (s, 6H, 2CH3). Anal. Found (calcd) for $C_{31}H_{23}F_6N_9O_6RuS_2 \cdot 5H_2O$: C, 37.63 (37.73); N, 12.59 (12.77); H, 2.77 (3.37). High-resolution MS (ESI, m/z): 748.0640 (M+).

[Ru(tpy)(bpm)(OH$_2$)](PF6)$_2$

1H NMR ($D_2O$, 400 MHz, as [Ru(tpy)(bpm)(D$_2$O)] $(PF_6)_2$): δ 9.83 (d, 1H), 9.25 (d, 1H), 8.60 (dd, 1H), 8.52 (d, 2H), 8.38 (d, 2H), 8.19 (t, 1H), 8.15 (t, 1H), 7.91 (t, 2H), 7.77 (d, 2H), 7.73 (dd, 1H), 7.27 (t, 2H), 7.08 (t, 1H). Anal. Found (calcd) for $C_{23}H_{19}F_{12}N_7OP_2Ru \cdot H_2O$: C, 33.72 (33.75); N, 12.09 (11.98); H, 2.54 (2.59).

[Ru(Mebimpy)(N—N)(OH$_2$)](OTf)$_2$

The aquo complexes were generated in situ by dissolving the triflate complexes in water.

[Ru(Mebimpy)(bpy)(OH$_2$)](OTf)$_2$

UV-vis λmax, nm (ϵ, $M^{-1}$ $cm^{-1}$): in 0.1 M HNO$_3$, 487 (12600), 358 (40460), 343 (34700), 315 (27150), 290 (46300), 253 (sh, 32000), 245 (34700); in 0.01 M NaOH, 600 (sh, 3970), 518 (11620), 357 (39500), 342 (33050), 315 (24450), 292 (50500), 255 (sh, 26650), 241 (31770).

[Ru(tpy)(bpm)(OH2)](PF6)2

UV-vis λmax, nm (ϵ, $M^{-1}$ $cm^{-1}$): in 0.1 M HNO$_3$, 483 (7350), 428 (sh, 6220), 365 (7050), 332 (sh, 14720), 309 (29900), 270 (sh, 26500), 262 (27900), 240 (30900), 231 (sh, 29800); in 0.01 M NaOH, 521 (7390), 477 (sh, 6660), 384 (8130), 316 (27600), 274 (23300), 263 (sh, 25800), 237 (34900).

Example 1

Reaction of [Ru(tpy)(C$_2$O$_4$)(OH$_2$)] with bpz or bpm in 0.1 M HClO$_4$ or of [Ru(tpy)(L)(Cl)]$^+$ (L is bpm or bpz) with AgNO$_3$ in 1:1 H$_2$O/MeOH yields the corresponding aqua complexes [Ru-(tpy)(bpz)(OH$_2$)]$^{2+}$ and [Ru(tpy)(bpm) (OH$_2$)]$^{2+}$.

[Ru(tpy)(bpz)(OH$_2$)]$^{2+}$ and [Ru(tpy)(bpm)(OH$_2$)]$^{2+}$ may be prepared according to methods discussed in the Concepcion et al., *J. Am. Chem. Soc.*, 2008, 130 (49), 16462-16463.

Example 2

The preparation of 1 [Ru(Mebimpy)(bpy)(OH$_2$)]$^{2+}$ (Mebimpy is 2,6-bis(1-methylbenzimidazol-2-yl)pyridine) and [Ru(Mebimpy)(4,4'-((HO)$_2$OPCH$_2$)$_2$bpy)(OH$_2$)]$^{2+}$ (1-PO$_3$H$_2$) is illustrated below. Ru(Mebimpy)Cl$_3$ is allowed to react with bpy or 4,4'-((EtO)$_2$OPCH$_2$)$_2$bpy in 2:1 EtOH: H$_2$O in the presence of NEt$_3$ giving [Ru(Mebimpy)(L)(Cl)]$^+$ (L is bpy or 4,4'-((EtO)$_2$OPCH$_2$bpy). The chloride ligand was subsequently displaced by the more labile triflate anion in neat triflic acid. Upon addition of water, rapid aquation occurs and the resulting aqua complex was isolated as the triflate salt by addition of excess lithium triflate. For the phosphonate ester precursor of 1-PO$_3$H$_2$, L=4,4'-((EtO)$_2$OPCH$_2$)$_2$bpy, the ester groups were hydrolyzed by heating the complex in 4.0 M aqueous HCl at 100° C. for 4 days prior to replacement of the chloride ligand.

Example 3

As shown in FIG. 1, the bpm complex shares with [Ru(tpy) (bpy)(OH$_2$)]$^{2+}$ multiple, pH-dependent oxidations in aqueous solutions. For [Ru(tpy)(bpy)(OH$_2$)]$^{2+}$, pH dependent $Ru^{III}/Ru^{II}$ and $Ru^{IV}/Ru^{III}$ couples appear separated by 92 mV over a broad pH range characteristic of closely spaced Ru(III/II) and Ru(IV/III) couples. The small potential separation between couples is a consequence of "redox potential leveling" and the PCET nature of the couple. Protons are lost with no build up of charge between couples, and higher oxidation state Ru(IV) is stabilized by RudO bond formation. There is no evidence for further oxidation of this complex to the solvent limit at ~1.8 V, and this complex is not a catalyst for water oxidation.

For [Ru(tpy)(bpm)(OH$_2$)]$^{2+}$, $Ru^{III}$ is a "missing" oxidation state. A single 2e⁻ $Ru^{IV}/Ru^{II}$ wave, as shown by peak current comparisons with the [Ru(bpy)$_3$]$^{3+/2+}$ couple, is observed from pH 0 to pH=14 with a change from the [Ru$^{IV}$=O]$^{2+}$+ 2e⁻+2H⁺→[Ru$^{II}$—OH$_2$]$^{2+}$ couple to [Ru$^{IV}$=O]$^{2+}$+ 2e⁻+H⁺→[Ru$^{II}$—OH]⁺, past p$K_{a,1}$=9.7. $E_{1/2}$ for the Ru$^{IV}$/ Ru$^{III}$ couple is lower than $E_{1/2}$ for the Ru$^{III}$/Ru$^{II}$ couple owing to bpm stabilization of Ru(II) by backbonding and stabilization of Ru(IV) (and Ru(V), see FIG. 1) by σ donation.

As shown in FIG. 1, at higher potentials a pH-independent, 1e⁻ wave appears in the cyclic voltammogram at 1.65 V as a shoulder on the onset of a catalytic wave for water oxidation. The electrochemistry for [Ru(tpy)(bpz)(OH$_2$)]$^{2+}$ is similar to that for [Ru(tpy)(bpm)-(OH$_2$)]$^{2+}$ with redox potentials for the corresponding Ru(IV/II) and Ru(V/IV) couples shifted to higher potentials.

Example 4

Figure 5:
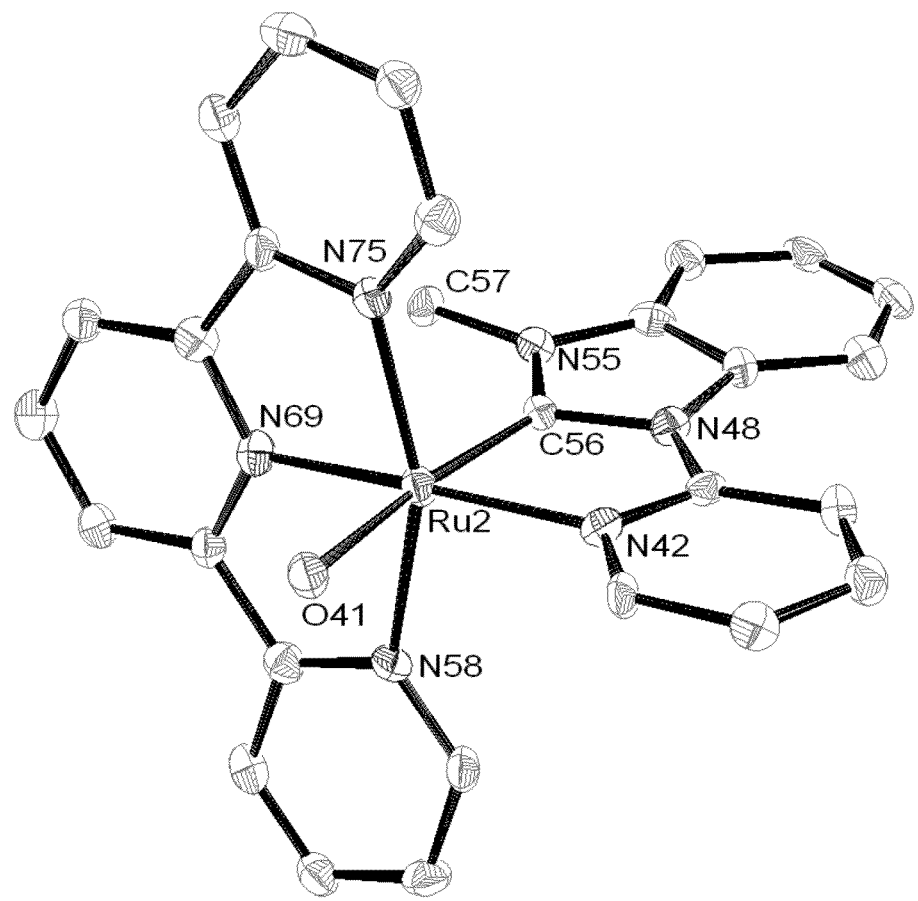
FIG. 5 shows the X-ray structure of the trans-$[Ru(tpy)(Mebim-py)(OH_2)]^{2+}$ cation in the salt trans-$[Ru(tpy)(Mebim-py)(OH_2)](ClO_4)_2$.

The crystal structure of trans-[Ru(tpy)(Mebim-py)(OH$_2$)]$^{2+}$ cation is shown in FIG. 5. Only one of the two possible isomers, the trans isomer, is obtained. Notable features in the structure are the relatively short Ru—C distance (1.943 Å) indicative of multiple Ru—C bonding and the longer Ru—O distance (2.183 Å) compared to Ru(tpy)(bpy)(OH$_2$)$^{2+}$ (2.146 Å) and Ru(tpy)(phendione)(OH$_2$)$^{2+}$ (2.127 Å, phendione is 1,10-phenanthroline-5,6-dione). (See Qvortrup et al., *Acta Crystallogr. Sect. E Struct. Rep. Online*, 2007, E63(5), m1400-m1401 and Fujihara, et al., *Dalton Trans.* 2004, 4, 645-652). This labializing effect might play an important role in the oxygen evolution step in the water oxidation catalytic cycle.

Example 5

Figure 6A:
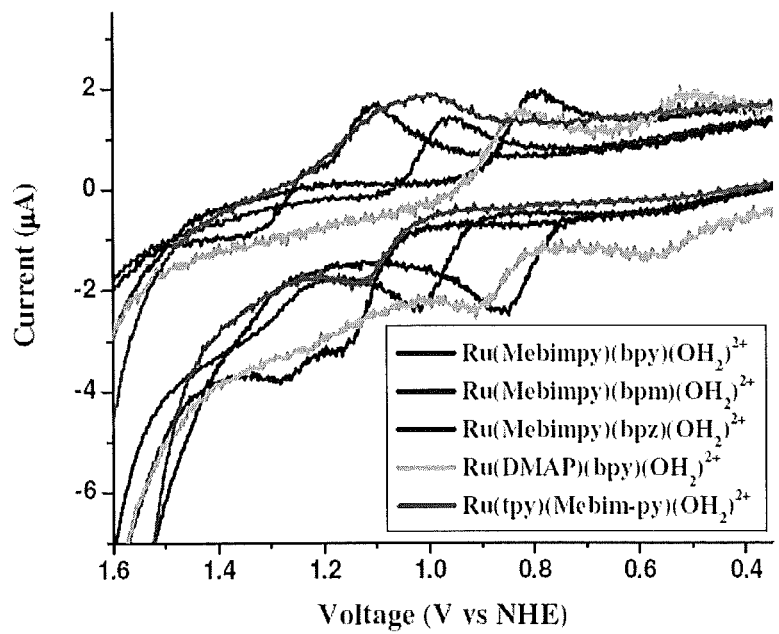
FIG. 6(a) demonstrates the representative cyclic voltammograms for monomeric catalysts when the conditions are 1.0 mM complex in 0.1 M $HNO_3$; glassy carbon working electrode; and scan rate: 10 mV/s.
Figure 6B:
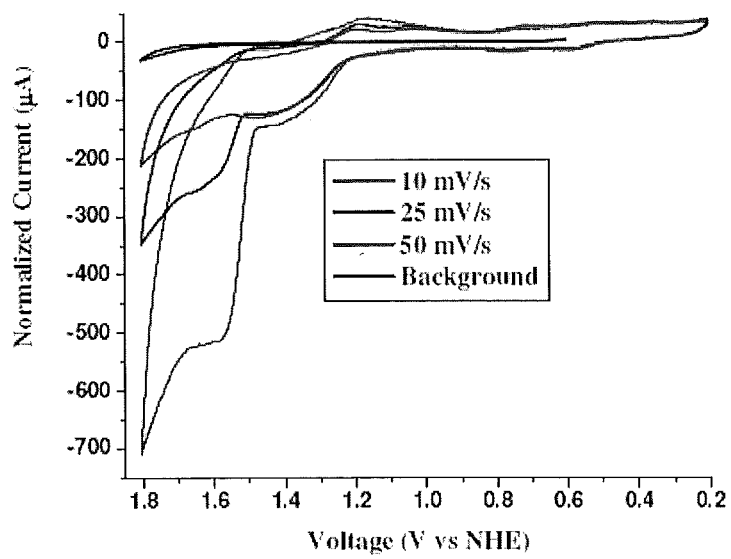
FIG. 6(b) shows cyclic voltammograms for $[Ru(tpy)(acac)(OH_2)]^+$ when the conditions are 1.0 mM complex in 0.1 M $HNO_3$ and glassy carbon working electrode.

Representative cyclic voltammograms for the series [Ru(Mebimpy)(LL)(OH$_2$)]$^{2+}$ (LL=bpy, bpm, bpz) and for Ru(D-MAP)(bpy)(OH$_2$)$^{2+}$ and trans-[Ru(tpy)(Mebim-py)-(OH2)]$^{2+}$ in 0.1 M HNO$_3$ and for Ru(tpy)(acac)(OH$_2$)]$^+$ are shown in FIGS. 6(*a*) and 6(*b*) respectively.

In these cyclic voltammograms, E$^{o'}$ values for the [Ru$^{III}$(Mebimpy)(LL)(OH/OH$_2$)]$^{2+/3+}$/[Ru$^{II}$(Mebimpy)(LL)-(OH$_2$)]$^{2+}$ and [Ru$^{IV}$(Mebimpy)(LL)(O)]$^{2+}$/[Ru$^{III}$(Mebimpy)-(LL)(OH/OH$_2$)]$^{2+/3+}$ couples vary systematically through the series from 0.82 to 1.13V for the Ru$^{III/II}$ couple and from 1.24 to 1.48 V for the Ru$^{IV/III}$ couple. E$^{o'}$ values for the Ru$^{III/II}$ and Ru$^{IV/III}$ couples vary from 0.51 to 1.18 V and from 0.74 to 1.54 V, respectively, in the entire series (Tables 1 and 2).

Variations in E$^{o'}$ are a consequence of the influence of σ-donor ligands in stabilizing higher oxidation states and π-acceptor ligands in stabilizing Ru$^{II}$, Ligand variations also influence the pK$_a$'s of Ru$^{III}$OH$_2$$^{3+}$ and Ru$^{II}$OH$_2$$^{2+}$, which, in turn, affect the redox potentials due to the Ph dependence of the Ru$^{III/II}$ and Ru$^{IV/III}$ couples. An additional Ru$^{V/IV}$, ligand-dependent wave appears as a shoulder from ~1.40 to ~1.72 V at the onset of a catalytic water oxidation wave. Electrocatalytic water oxidation waves well above the background appear for all complexes past 1.3 V.

TABLE 1

Water Oxidation Rate Constants and E$_{1/2}$ (V vs NHE) Values for the Ru$^{III/II}$, Ru$^{IV/III}$, and Ru$^{V/IV}$ Couples in the Series [Ru(tpy)(LL)(OH$_2$)]$^{n+}$ in 0.1M HNO$_3$$^a$

| LL | R$^{III/II}$ | Ru$^{IV/III}$ | Ru$^{V/IV}$ | k$_{O—O}$ or k$_4$ (s$^{-1}$) | k$_2$ or k$_5$ (M$^{-1}$ s$^{-1}$) | t$_{1/2}$ (s$^{-1}$) |
|---|---|---|---|---|---|---|
| bpy | 1.01 | 1.19 | 1.60 | 1.9 × 10$^{-4}$ | | 3650 |
| bpm | 1.12 | <1.12 | 1.65 | 7.5 × 10$^{-4}$ | | 925 |
| bpz | 1.22 | <1.22 | 1.69 | 1.4 × 10$^{-3}$ | | 495 |
| Mebim-py | 1.11 | 1.49 | 1.70 | | 33 | 410 |
| Mebim-pz | 1.18 | 1.54 | 1.72 | | 170 | 80 |
| acae | 0.51 | 1.14 | 1.58 | 5.0 × 10$^{-4}$ | 515 | 1390.26 |

$^a$Half-times (t$_{1/2}$) for net Ce$^{IV}$ consumption with [Ce$^{IV}$] = 1.5 × 10$^{-3}$M and [RuOH$_2$]$^{2+}$ - 5.1 × 10$^{-5}$M at 23 ± 2° C. Only 2e$^-$Ru$^{IV}$=O$^{2+}$/Ru$^{II}$OH$_2$$^{2+}$ couples are observed for [Ru(tpy)(LL)(OH$_2$)]$^{n+}$(LL = bpm, bpz).

TABLE 2

As in Table 1 for the Series[Ru(LLL)(bpy)(OH$_2$)]$^{2+}$

| LLL | Ru$^{III/II}$ | Ru$^{IV/III}$ | Ru$^{V/IV}$ | k$_4$ (s$^{-1}$) | k$_2$ or k$_5$ M$^{-1}$ s$^{-1}$ | t$_{1/2}$ (s$^{-1}$) |
|---|---|---|---|---|---|---|
| tpy | 1.01 | 1.19 | 1.60 | 1.9 × 10$^{-4}$ | | 3650 |
| Mebimpy | 0.82 | 1.29 | 1.67 | | 52 | 260 |
| DMAP | 0.54 | 0.88 | 1.40 | | 4.1 | 3315 |

Example 6

Some complexes were screened as catalysts for net water oxidation by Ce$^{IV}$, 2H$_2$O+4Ce$^{4+}$→O$_2$+4H$^+$+4Ce$^{3+}$, by adding 30 equivalents of Ce$^{IV}$ to 5.1×10$^{-5}$ M complex in 0.1 M HNO$_3$. In these experiments loss of Ce$^{IV}$ was monitored spectrophotometically at 360 nm, on the shoulder of λ$_{max}$ 318 nm for Ce$^{IV}$, ε=3070 M$^{-1}$cm$^{-1}$. In all cases complete Ce$^{IV}$ consumption was observed on time scales from <100 s to 20000 s.

For the series [Ru(tpy)(LL)(OH$_2$)]$^{n+}$ (Table 1; LL=bidentate ligand) and [Ru(LLL)(bpy)(OH$_2$)]$^{2+}$ (Table 2; LLL=tpy, Mebimpy, or DMAP) in 0.1 M HNO$_3$, absorbance-time measurements with Ce$^{IV}$ in pseudo-first-order excess revealed two types of behavior. In one, the rate law was first-order in complex, added initially as Ru$^{II}$(OH$_2$)$^{n+}$, and zero-order in Ce$^{4+}$. The initial oxidation to Ru$^{IV}$=O$^{n+}$ is rapid. According to the mechanism described in the application, this behavior is consistent with either rate-limiting Ru$^{IV}$=O$^{n+}$ oxo attack on H$_2$O, k$_{O—O}$, or rate-limiting O$_2$ loss from Ru$^{IV}$(OO)$^{n+}$, k$_4$. The latter is rate-limiting for [Ru(tpy)(bpm)(OH$_2$)]$^{2+}$- and [Ru(tpy)(bpz)(OH$_2$)]$^{2+}$-catalyzed water oxidation. In the second type of behavior, the rate law was first-order in [Ru$^{II}$(OH$_2$)$^{2+}$] and first-order in Ce$^{4+}$. This limit is consistent with either rate-limiting oxidation of Ru$^{IV}$=O$^{n+}$ to Ru$^V$=O$^{(n+1)+}$, k2 in the mechanism proposed in the application, or rate-limiting oxidation of Ru$^{IV}$(OO)$^{n+}$, k5. [Ru(tpy)(acac)(OH$_2$)]$^+$ is different. Both first- and zero-order pathways in CeIV compete in 0.1 M HNO$_3$, with the first-order pathway dominating early in the catalytic cycle and the zero-order pathway dominating as Ce$^{IV}$ is depleted.

Tables 1 and 2 present E$_{1/2}$ values for Ru$^{III/II}$, Ru$^{IV/III}$, and Ru$^{V/III}$ couples as well as rate constants for the rate-limiting steps in water oxidation catalysis by the series [Ru(tpy)-(LL)(OH$_2$)]$^{n+}$ and [Ru(LLL)(bpy)(OH$_2$)]$^{2+}$. For comparisons among catalysts having different rate-limiting steps, the half times t$_{1/2}$ for consumption of Ce$^{IV}$, with Ce$^{IV}$=1.5×10$^{-3}$ M initially and [Ru(OH$_2$)]$^{n+}$=5.1×10$^{-5}$, are also reported.

General trends emerge from the data in Tables 1 and 2. For the Ru$^{V/III}$ couples, of relevance in the O—O bond-forming step (k$_{O—O}$ in the proposed mechanism), E$_{1/2}$(Ru$^{V/III}$)=½[(E$_{1/2}$(Ru$^{V/IV}$)+E$_{1/2}$ (R$^{IV/III}$)], is dictated largely by the Ru$^{V/III}$ couple. It is highly tunable ranging from 1.54 to 0.88 V because of its sensitivity to the σ-donor and π-acceptor properties of the ligands. The Ru$^{V/III}$ couple is pH-dependent. E$^{o'}$ decreases by −118 mV/pH unit in strongly acidic solutions where the Ru$^V$=O$^{n+}$/Ru$^{III}$OH$_2$$^{2+}$ couple and by −59 mV/pH unit for the Ru$^V$=O$^{n+}$/Ru$^{III}$OH$^{(n-1)+}$ couple dominates past the pK$_a$ for Ru$^{III}$OH$_2$$^{n+}$, which is also ligand-dependent.

For representative complexes [Ru(tpy)(bpm)(OH$_2$)]$^{2+}$, [Ru(tpy)(Mebim-py)(OH$_2$)]$^{2+}$, [Ru(tpy)(Mebim-pz)(OH$_2$)]$^{2+}$, and [Ru(Mebimpy)(bpy)(OH$_2$)]$^{2+}$, oxygen evolution was measured by use of an O$_2$ electrode. In all cases, the expected amount of oxygen, 7.5 equiv/30 equiv of Ce$^{IV}$, was observed, showing that water oxidation is quantitative.

Example 7

Stable phosphonate surface binding of 1-PO$_3$H$_2$ ([Ru(Mebimpy)(4,4'-((HO)$_2$OPCH$_2$)$_2$bpy)(OH$_2$)]$^{2+}$) on FTO (fluorine-doped $SnO_2$) or ITO (Sn(IV)-doped $In_2O_3$) and in optically transparent films (~10 μm thickness) of nanoparticle $TiO_2$ (10-20 nm diameter) on FTO (FTO|$TiO_2$) occurred following exposure of the electrodes to a 0.1 mM stock solution of 1-$PO_3H_2$ in methanol.

The schematic representation of {Ru(Mebimpy)[4,4'-((HO)$_2$OPCH$_2$)$_2$bpy](OH$_2$)}$^{2+}$ (1-$PO_3H_2$) attached on a metal oxide B was show below:

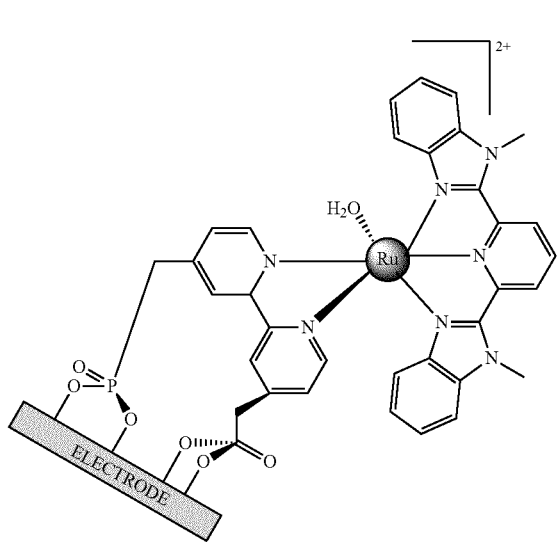

Figure 7A:
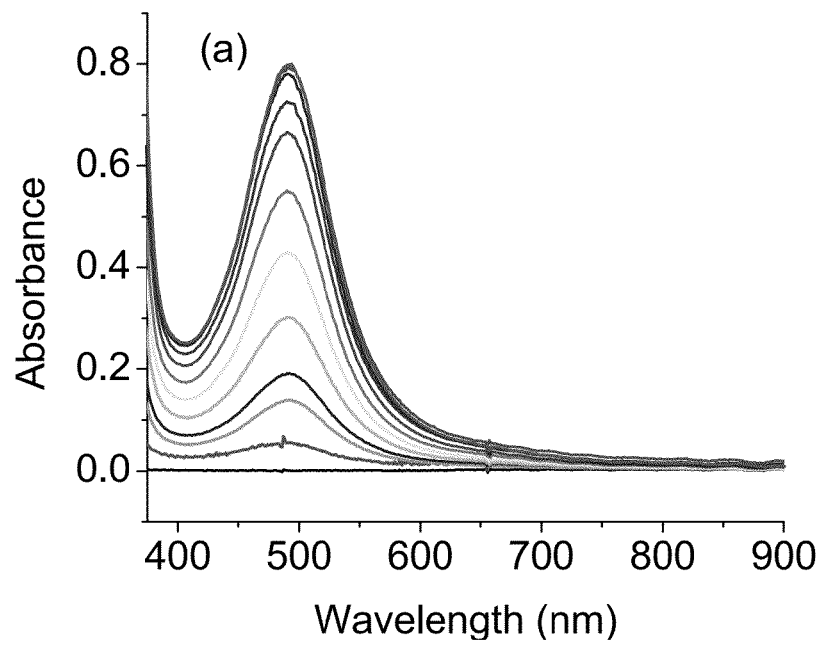
FIG. 7(a) shows UV-vis spectra of FTO|TiO$_2$|1-PO$_3$H$_2$ after various soaking times in 0.1 mM solution in methanol.
Figure 7B:
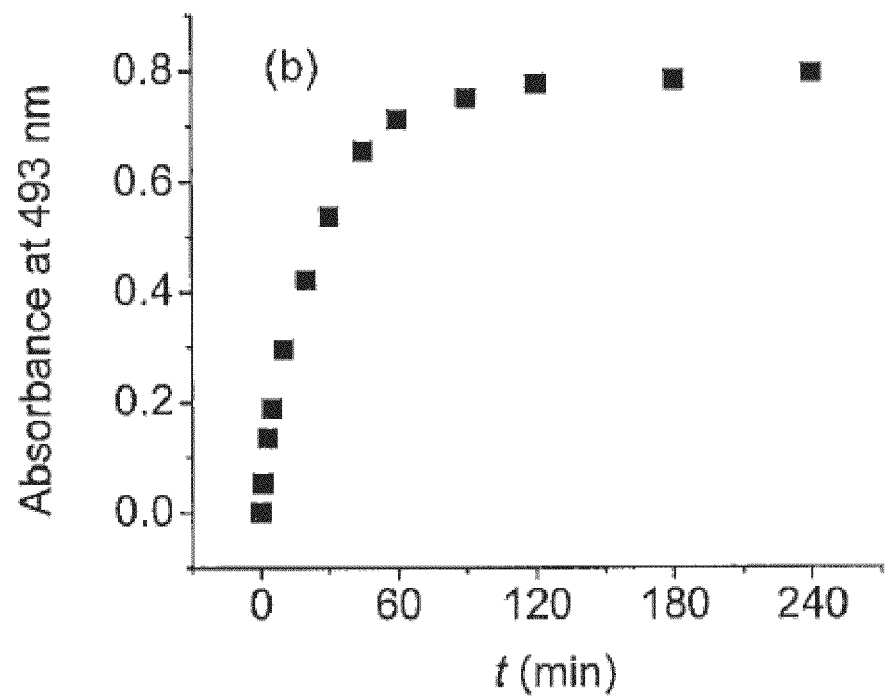
FIG. 7(b) shows the dependence of the absorbance at 493 nm on the soaking time.
Figure 20:
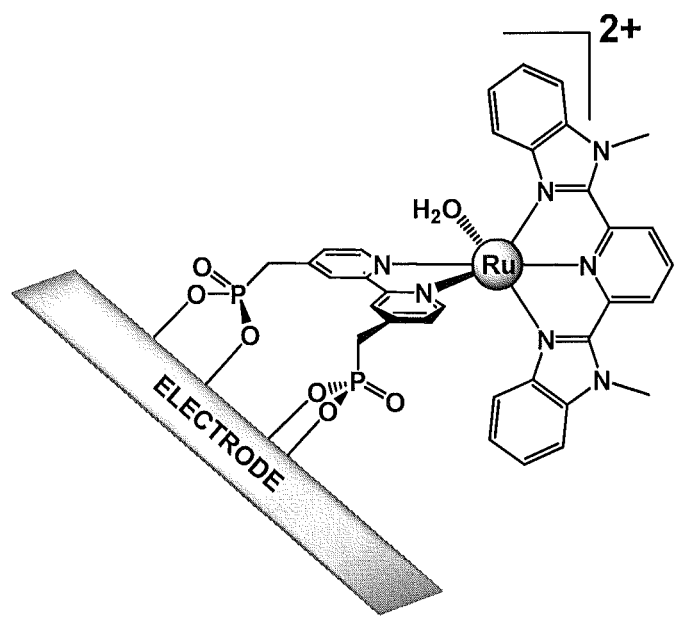
FIG. 20 illustrates schematic representation of 1-$PO_3H_2$ attached to a metal oxide electrode.
Figure 21:
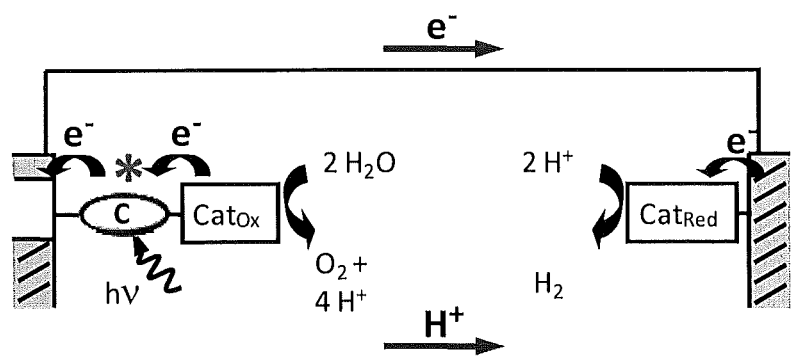
FIG. 21 illustrates a proposed photoelectrochemical cell (PEC) for water splitting. C is a chromophore, D an electron transfer donor, A an electron transfer acceptor and $Cat_{ox}$ and $Cat_{Red}$ are catalysts for water oxidation and reduction.

Saturation coverage of $1.2 \times 10^{-10}$ mol/cm$^2$ on FTO and ITO was achieved in ~2 h as monitored by the area under the cyclic voltammetric wave for the Ru(III/II) couple at $E_{1/2}$=0.67 V vs NHE in pH 5 ($CH_3CO_2H/CH_3CO_2Na$ buffer, I=0.1 M), Figure S1. The extent of surface loading on FTO|$TiO_2$ in mol/cm$^2$ was calculated from UV-visible measurements by using $\Gamma = A(\lambda)/(10^3 \times \epsilon(\lambda))$, with $A(\lambda)$ and $\epsilon(\lambda)$ the absorbance and molar absorptivities at $\lambda$. (See Trammell et al., *J. Phys. Chem. B*, 1999, 103(1), 104-107.) For surface-bound Ru$^{II}$—OH$_2^{2+}$, $\lambda_{max}$=493 nm and $\epsilon_{max}$=1.5×10$^4$ M$^{-1}$cm$^{-1}$ for 1-$PO_3H_2$ in methanol was used for $\epsilon(\lambda)$. Typical saturated surface coverage after 4 h exposure times were 5.3×10$^{-8}$ mol/cm$^2$ for FTO|$TiO_2$ (See FIGS. 7(a) and (b)). In addition, the schematic representation of 1-$PO_3H_2$ attached to a metal oxide electrode is shown in FIG. 20.

Example 8

Figure 8:
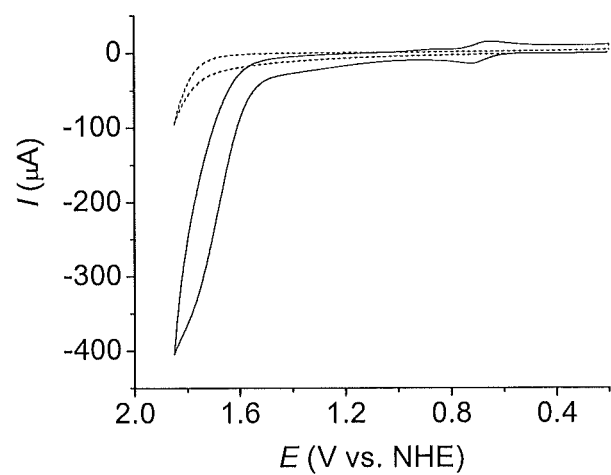
FIG. 8 demonstrates cyclic voltammogram of 1 mM of $[Ru(Mebimpy)(bpy)(OH_2)]^{2+}$ 1 at pH 5 at GC electrode (I=0.1 M, $CH_3CO_2H/CH_3CO_2Na$; scan rate, 100 mV/s). The dotted line is the solution blank under the same experimental conditions.
Figure 9A:
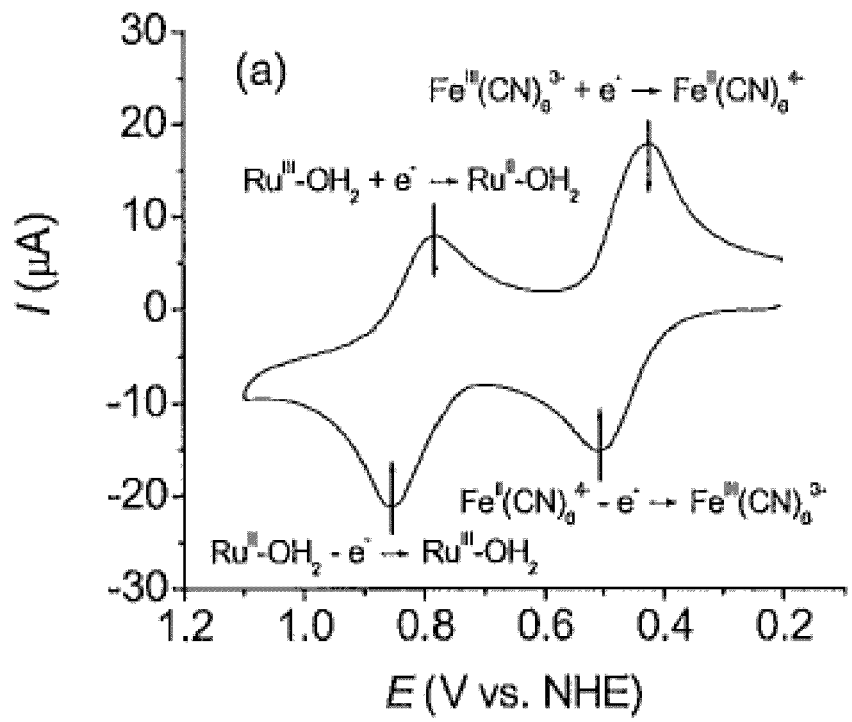
FIG. 9(a) demonstrates cyclic voltammogram of a mixture of 1 mM of $[Ru(Mebimpy)(bpy)(OH_2)]^{2+}$ 1 and 1 mM $Fe(CN)_6^{4-}$ in solution at pH 2 comparing peak currents for the one-electron waves for the corresponding Ru(III/II) and $Fe(CN)_6^{3-/4-}$ couples.
Figure 9B:
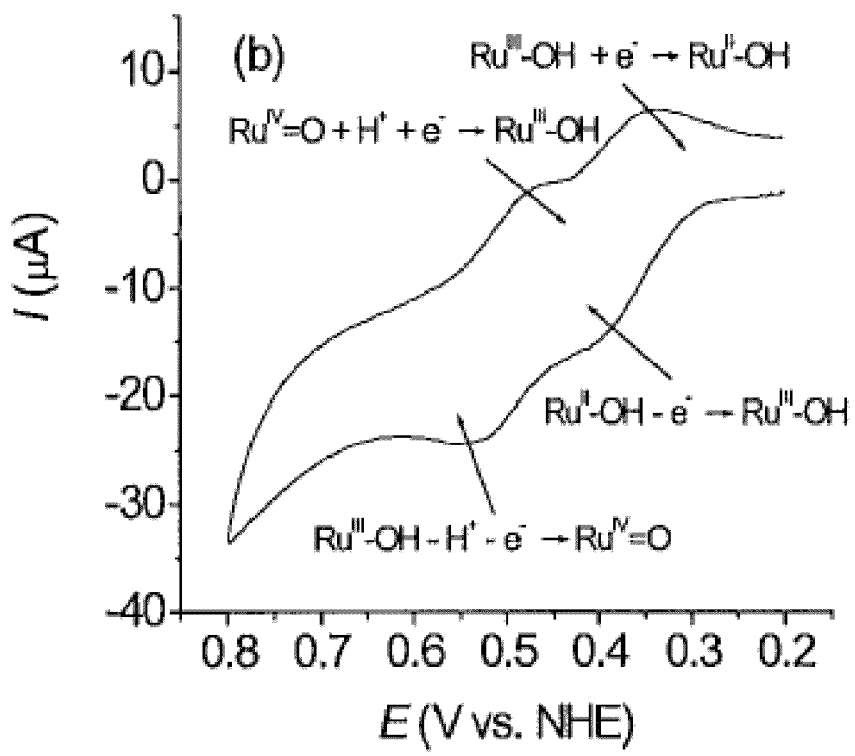
FIG. 9(b) demonstrates cyclic voltammogram of 1 mM of $[Ru(Mebimpy)(bpy)(OH_2)]^{2+}$1 at pH 14 showing the one-electron waves for the Ru(IV/III) and Ru(III/II) couples. I=0.1 M, $CH_3CO_2H/CH_3CO_2Na$; GC working electrode; scan rate, 100 mV/s.
Figure 10:
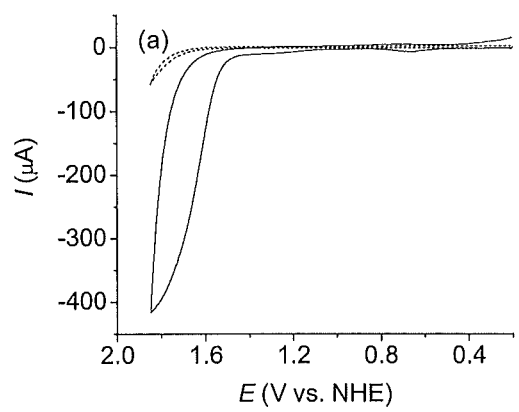
FIG. 10(a) demonstrates cyclic voltammogram of ITO|1-PO$_3$H$_2$ at pH 5 (I=0.1 M, $CH_3CO_2H/CH_3CO_2Na$; scan rate, 100 mV/s). The dotted line is the ITO background under the same experimental conditions.
FIG. 10(b) Cyclic voltammograms of ITO|1-PO$_3$H$_2$ at pH 5 before (solid line) and after (dotted line) scanning to 1.85 V.
Figure 10:
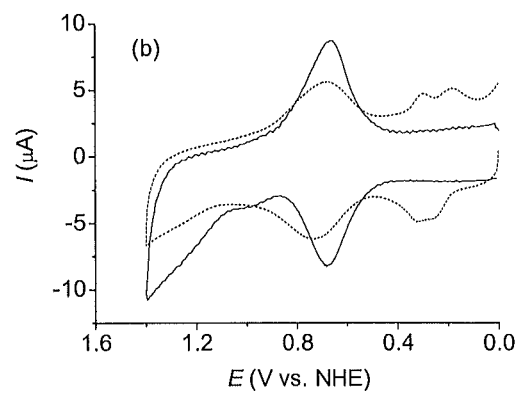
Figure 11:
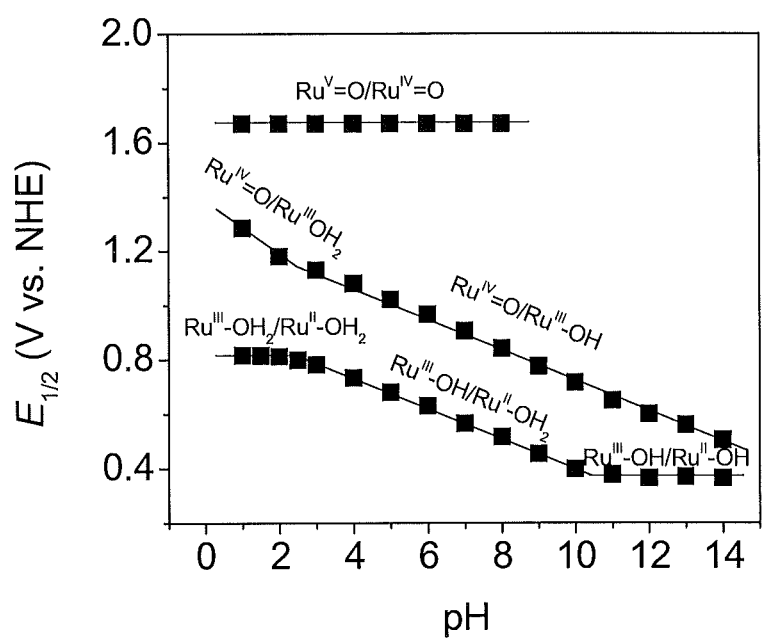
FIG. 11 demonstrates plots of $E_{1/2}$ vs pH for the Ru(III/II), Ru(IV/III), and Ru(V/IV) solution redox couples of $[Ru(Mebimpy)(bpy)(OH_2)]^{2+}$1 (I=0.1 M; GC working electrode; scan rate, 100 mV/s).
Figure 12:
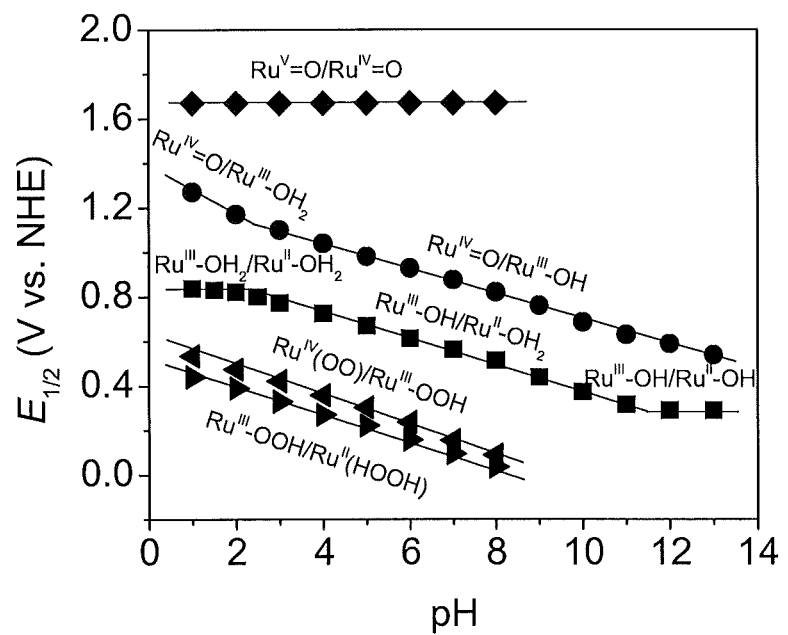
FIG. 12 demonstrates plots of $E_{1/2}$ vs pH for the Ru(III/II), Ru(IV/III), and Ru(V/IV) surface-bound couples at FTO|1-PO$_3$H$_2$ (or ITO|1-PO$_3$H$_2$) and for the peroxidic $Ru^{IV}(OO)^{2+}$/$Ru^{III}$-OOH$^{2+}$ and $Ru^{III}$-OOH$^{2+}$/$Ru^{II}$(HOOH)$^{2+}$ redox couples following an oxidative scan to 1.85 V vs NHE (I=0.1 M; scan rate, 100 mV/s).
Figure 15:
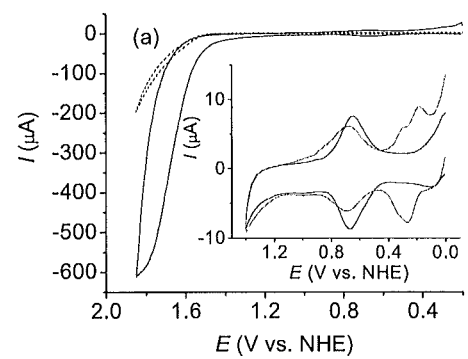
FIG. 15(a) shows the cyclic voltammogram of FTO|1-$PO_3H_2$ at pH 5 (I=0.1 M, $CH_3CO_2H/CH_3CO_2Na$; scan rate, 100 mV/s). The dotted line is the FTO background under the same experimental conditions. The inset shows cyclic voltammograms of FTO|1-$PO_3H_2$ at pH 5 before (blue line) and after (red line) scanning to 1.85 V.
FIG. 15(b) shows the electrolysis of FTO|1-$PO_3H_2$ at 1.85 V vs NHE at pH 5. Number of turnovers ~11,000, turnover frequency ~0.36 $s^{-1}$ (background subtracted). $\Gamma=1.2\times10^{-10}$ mol/$cm^2$, area=1.25 $cm^2$, current density ~14.8 $\mu A/cm^2$.
Figure 15:
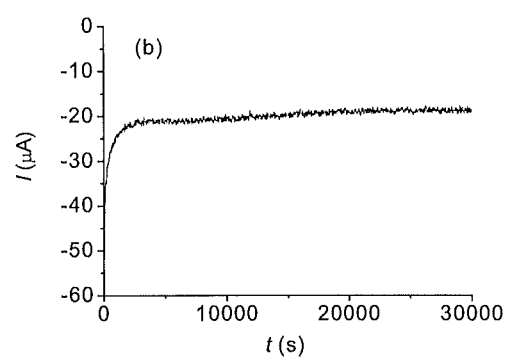

In FIG. 15a a cyclic voltammogram (CV) of FTO|1-$PO_3H_2$ at pH=5 ($CH_3CO_2H/CH_3CO_2Na$ buffer, I=0.1 M) is shown. As for solution couples in FIGS. 8 and 9, pH dependent waves appear for sequential Ru(III/II) and Ru(IV/III) couples on the surface at ~0.67 and 0.98 V. Peak currents vary with scan rate as expected for surface couples. A pH independent Ru(V/IV) wave appears at ~1.67 V on the onset of a catalytic water oxidation wave. Closely related results were obtained for ITO|1-$PO_3H_2$, FIG. 10. As observed earlier for a related surface couple, the Ru$^{IV}$=O$^{2+}$/Ru$^{III}$—OH$^{2+}$ wave is kinetically inhibited on the surface due to the proton demands of the couple.[9] It is more distinct at slow scan rates or at high pH, FIG. 9. $E_{1/2}$-pH plots for solution and surface couples are shown in FIGS. 11 and 12.

Figure 13A:
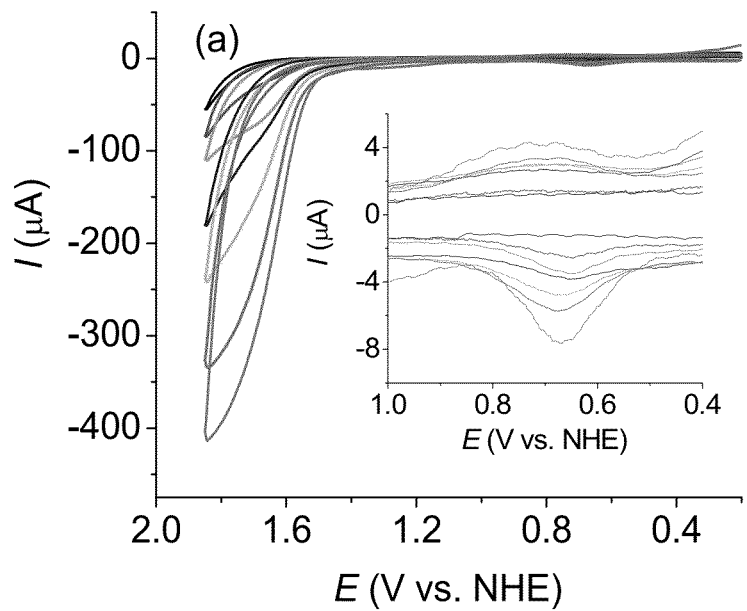
FIG. 13(a) demonstrates cyclic voltammograms for ITO|1-PO$_3$H$_2$ electrodes with various complex loadings at pH 5 (I=0.1 M, $CH_3CO_2H/CH_3CO_2Na$; scan rate, 100 mV/s). Inset shows a magnified view of anodic and cathodic waves for the Ru(III/II) surface couple.
Figure 13B:
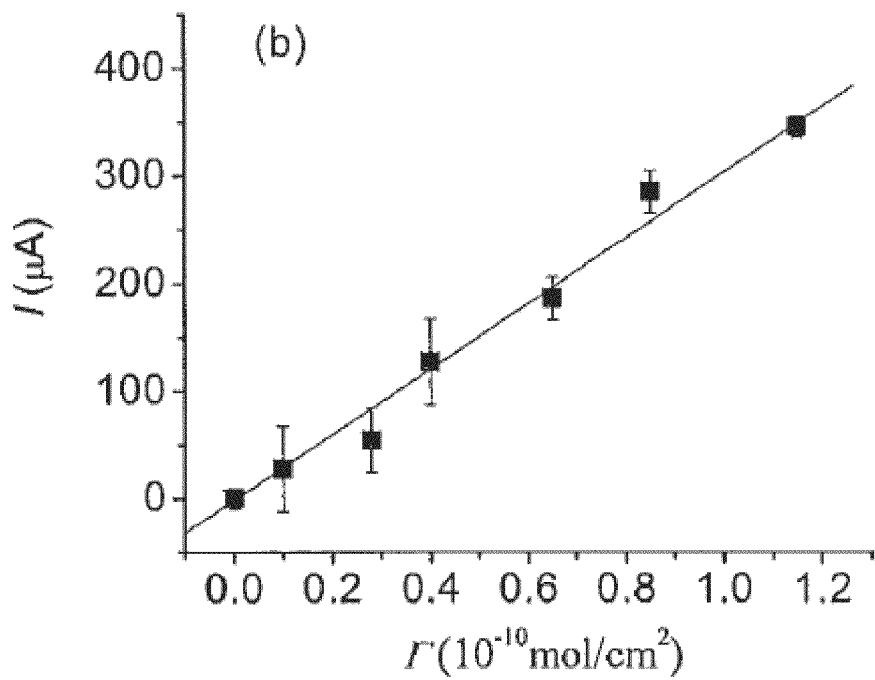
FIG. 13(b) shows the dependence of the electrocatalytic current at 1.85 V vs NHE on surface complex loading (ITO background subtracted).
Figure 14A:
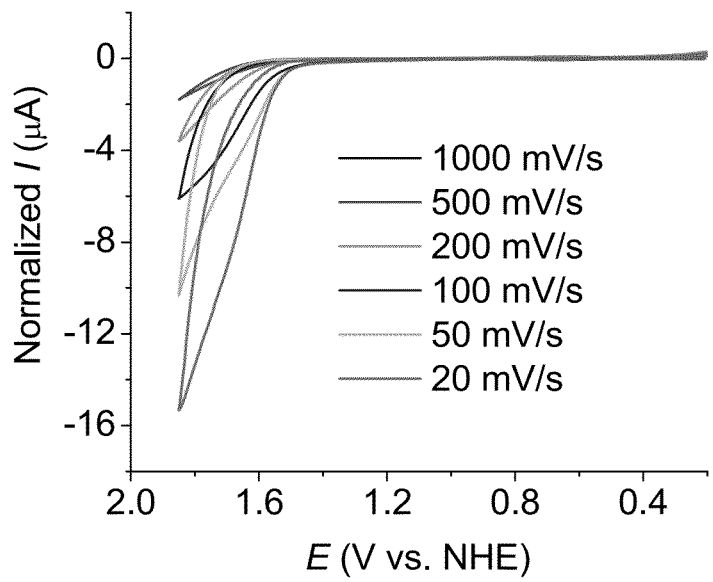
FIG. 14(a) demonstrates selective cyclic voltammograms of FTO|1-PO$_3$H$_2$ at pH 5 at different scan rates (I=0.1 M, $CH_3CO_2H/CH_3CO_2Na$). The currents are normalized for scan rate, i/v.
Figure 14B:
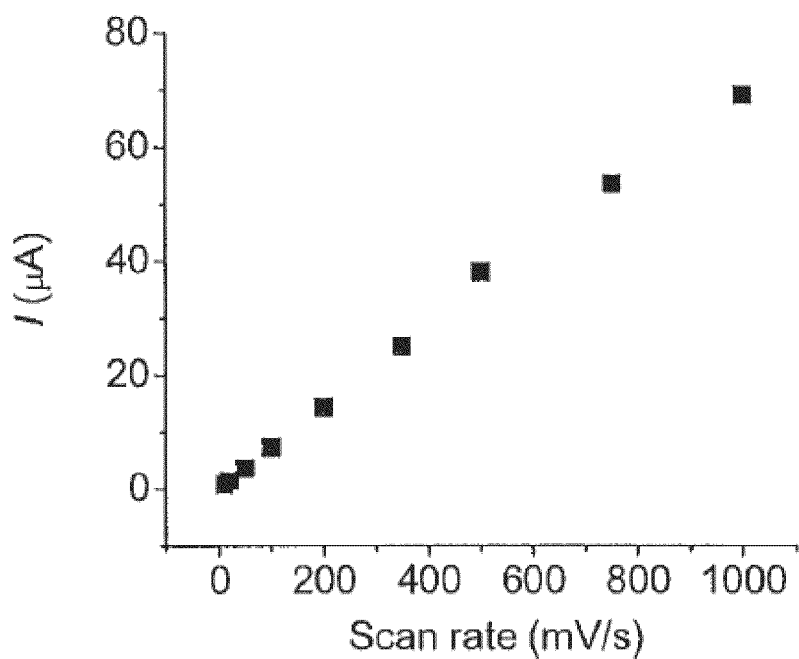
FIG. 14(b) demonstrates dependence of peak current on scan rate for the Ru(III/II) surface wave at $E_{1/2}$~0.67 V vs NHE.

The catalytic peak current at 1.85 V varies linearly with surface coverage, FIG. 13, consistent with a single site mechanism for water oxidation. When normalized for scan rate, the catalytic peak current increases with decreasing scan rate consistent with a rate limiting step prior to electron transfer to the electrode, FIG. 14.

Figure 16:
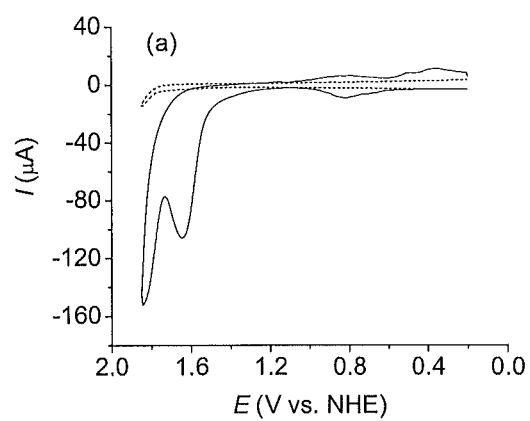
FIG. 16(a) shows the cyclic voltammogram of ITO|1-$PO_3H_2$ at pH 1 (0.1 M $HNO_3$; scan rate, 100 mV/s). The dotted line is the ITO background under the same experimental conditions.
FIG. 16(b) shows the electrolysis of ITO|1-$PO_3H_2$ at 1.85 V vs NHE at pH 1 (0.1 M $HNO_3$). Number of turnovers ~3600, turnover frequency ~0.12 $s^{-1}$ (background subtracted). $\Gamma=1.2\times10^{-10}$ mol/$cm^2$, area=1.25 $cm^2$, current density ~4.9 $\mu A/cm^2$.
Figure 16:
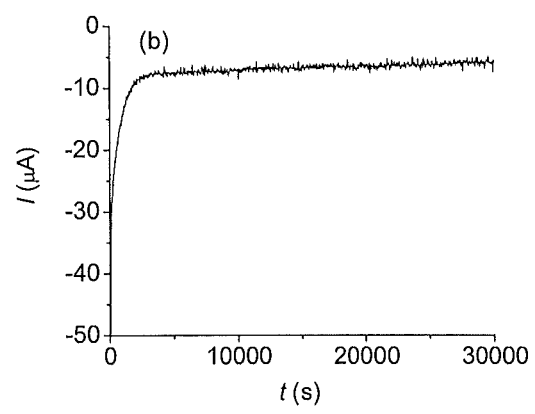

Stepping the applied potential to $E_{p,a}$=1.85 V at pH=5, results in sustained electrocatalytic water oxidation, FIG. 15b, with a current density of ~14.8 μA/cm$^2$. Catalysis was sustained for at least 8 h corresponding to ~11,000 turnovers at a turnover rate of ~0.36 s$^{-1}$. Sustained catalytic currents were also obtained at pH 1 (0.1 M HNO$_3$) with a current density of ~4.9 μA/cm$^2$, FIG. 16.

Example 9

Figure 3:
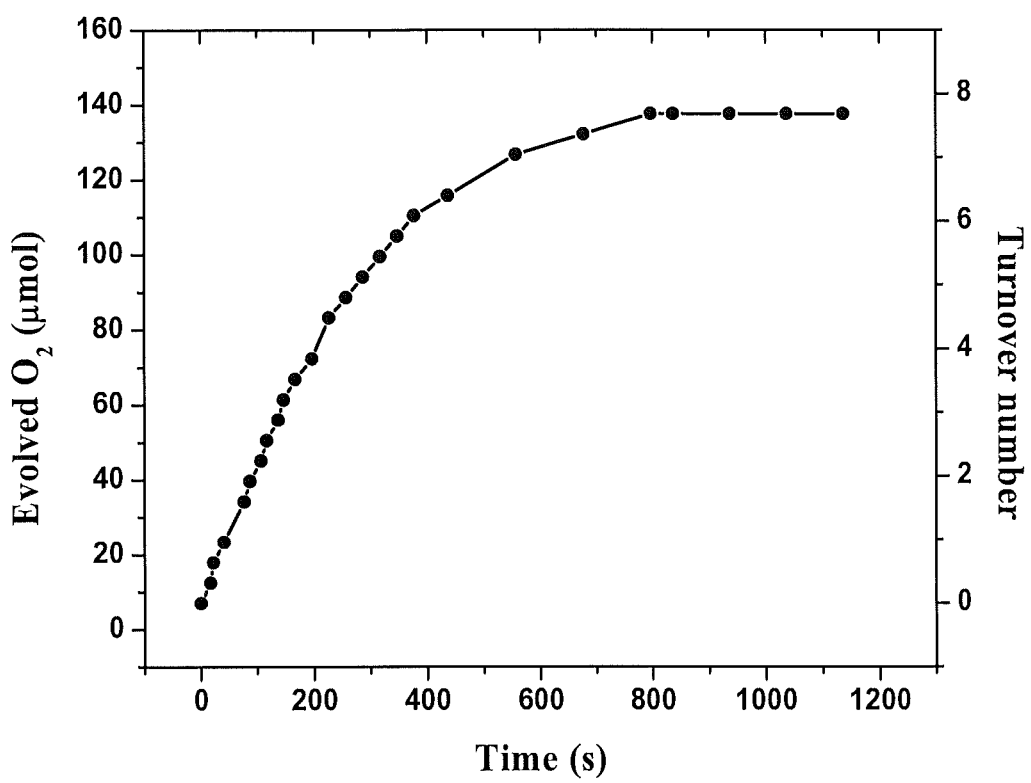
FIG. 3 graphically demonstrates plots of the amount of evolved ($O_2$) versus time and turnover number for $Ru(tpy)(bmp)(OH_2)]^{2+}$.
Figure 17:
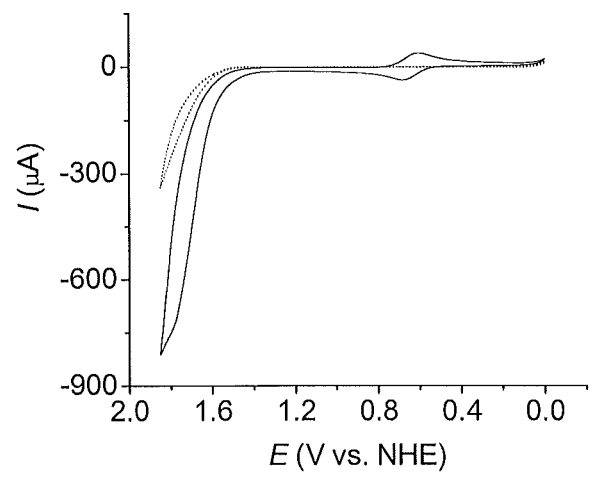
FIG. 17 demonstrates cyclic voltammogram of FTO|$TiO_2$|1-$PO_3H_2$ at pH 5 (I=0.1 M, $CH_3CO_2H/CH_3CO_2Na$; scan rate, 10 mV/s). The dotted line is the FTO|$TiO_2$ background under the same experimental conditions.
Figure 18A:
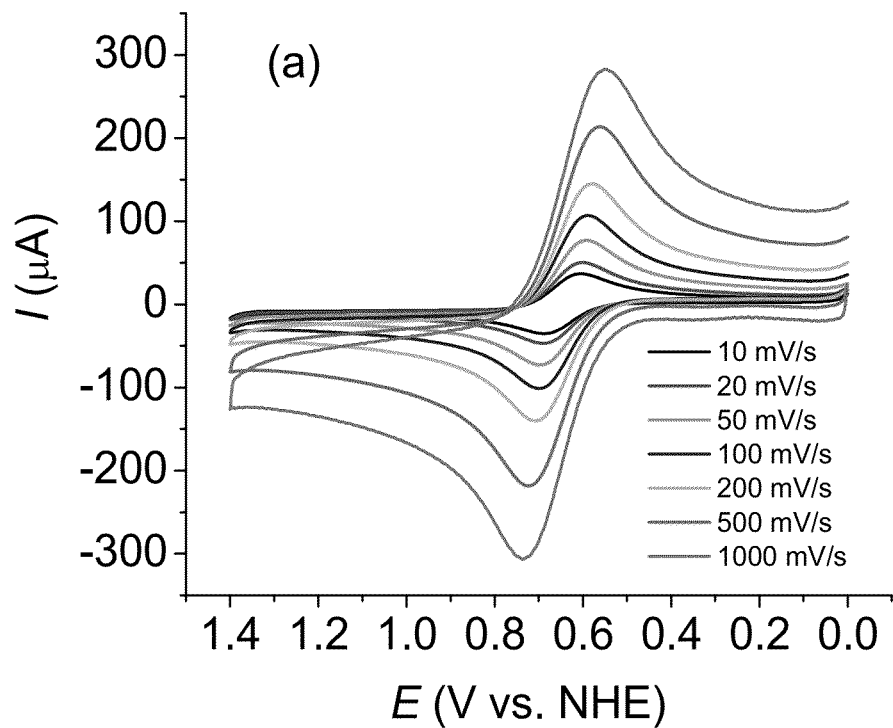
FIG. 18(a) illustrates cyclic voltammograms of FTO|$TiO_2$|1-$PO_3H_2$ at pH 5 at different scan rates (I=0.1 M, $CH_3CO_2H/CH_3CO_2Na$).
Figure 18B:
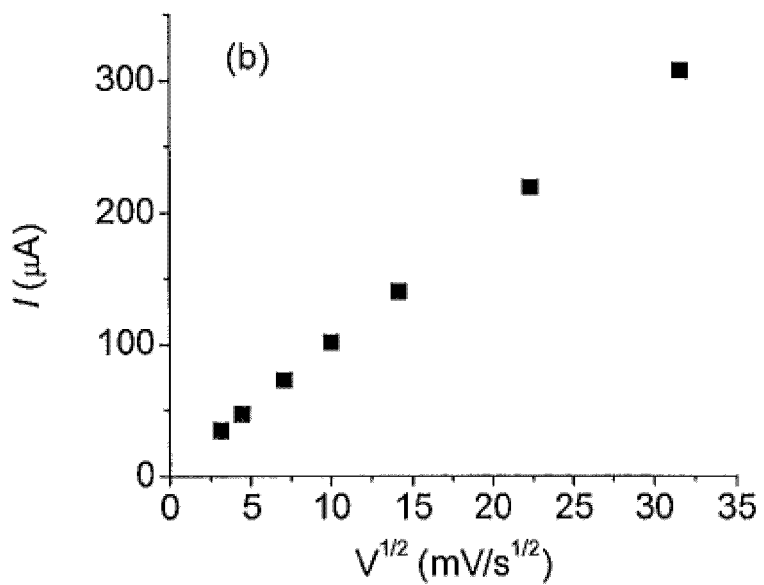
FIG. 18(b) shows dependence of the peak current for the Ru(III/II) wave on the square root of the scan rate.

The catalyst was also investigated on FTO|$TiO_2$. The same pattern of voltammetric waves was observed, FIG. 17. In cyclic voltammograms the peak current for the Ru(III/II) couple varied linearly with the square root of the scan rate, FIG. 18. This is consistent with an earlier observation for a surface-bound Os$^{II}$ complex[8] and electron transfer to and from the surface couple by cross-surface electron transfer. Based on peak current measurements, ~2.5% of the available sites were electroactive at a scan rate of 100 mV/s and ~8.0% at a scan rate of 10 mV/s. Complete oxidation occurs on longer time scales. As shown in FIG. 3, the spectrum of FTO|$TiO_2$|1-$PO_3H_2$ as Ru$^{II}$—OH$_2$ is dominated by a metal-to-ligand charge transfer (MLCT) absorption band at 493 nm. A potential hold experiment at 0.75 V at pH 5, past $E_{1/2}$ for the Ru$^{III}$—OH$^{2+}$/Ru$^{II}$—OH$_2^{2+}$ couple, results in spectral changes consistent with oxidation of Ru$^{II}$—OH$_2^{2+}$ to Ru$^{III}$—OH$^{2+}$ and, at 1.20 V, to oxidation of Ru$^{III}$—OH$^{2+}$ to Ru$^{IV}$=O$^{2+}$. A further increase in potential to 1.85 V results in spectral features for an intermediate similar to Ru$^{IV}$=O$^{2+}$, Ru$^{IV}$(OO)$^{2+}$, see below and note Scheme 1. Reduction of Ru$^{III}$—OH$^{2+}$, Ru$^{IV}$=O$^{2+}$, or Ru$^{IV}$(OO)$^{2+}$ past $E_{p,c}$ for the Ru$^{III}$—OH$_2^{2+}$ couple results in complete recovery of Ru$^{II}$—OH$_2^{2+}$.

Figure 19:
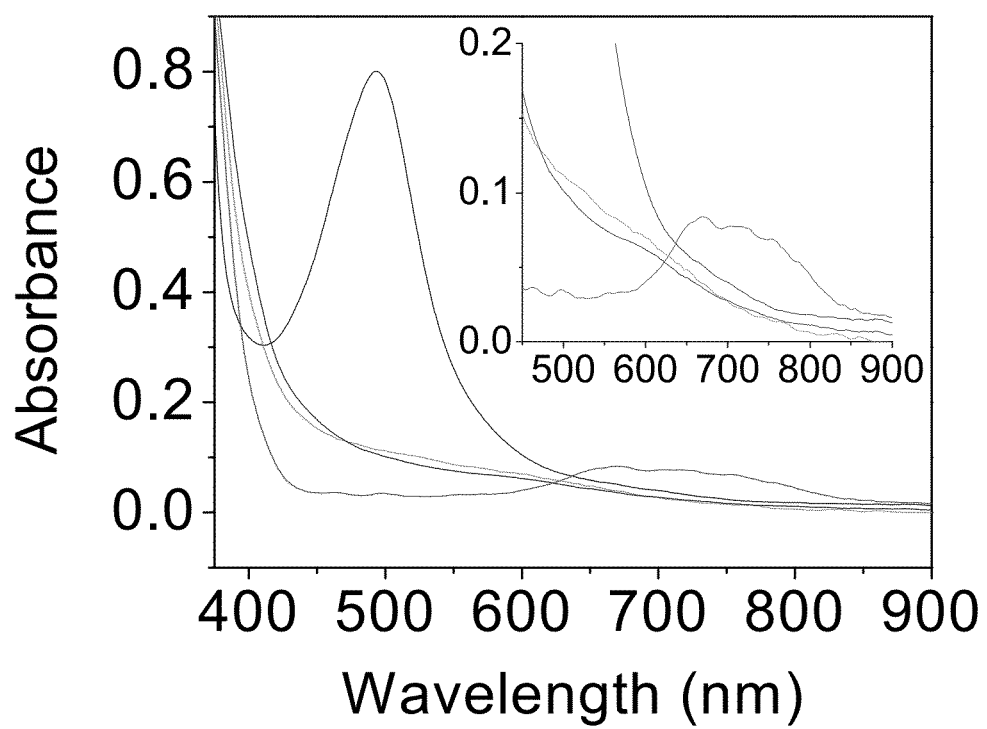
FIG. 19 demonstrates UV-Vis spectra of FTO|$TiO_2$|1-$PO_3H_2$ (black line), following complete electrolysis at: 0.75 V (red line, actual spectrum×4.5), 1.20 V (green line) and 1.85 V (blue line) vs NHE at pH 5. The spectrum in red was obtained with $\Gamma=0.26\times10^{-10}$ mol/$cm^2$, and the others with $\Gamma=1.2\times10^{-10}$ mol/$cm^2$. The inset shows a magnified view of the low energy visible.

The complex retains its electrocatalytic activity toward water oxidation on FTO|$TiO_2$. Electrolysis of FTO|$TiO_2$|1-$PO_3H_2$ at 1.85 V at pH 5 resulted in sustained electrocatalysis, FIG. 19. Water oxidation is slow on FTO|$TiO_2$|1-$PO_3H_2$ with a turnover rate of 0.004 s$^{-1}$ due to rate limiting cross-surface electron transfer. Comparison of the integrated current over a period of 30,000 s with measurement of oxygen evolution by an oxygen electrode (YSI ProODO™) gave 6.5 μmol of O$_2$ corresponding to an oxygen yield of 77%. Given the difficulties in the experiment, this represents a lower limit in the oxygen yield.

Example 10

Figure 22:
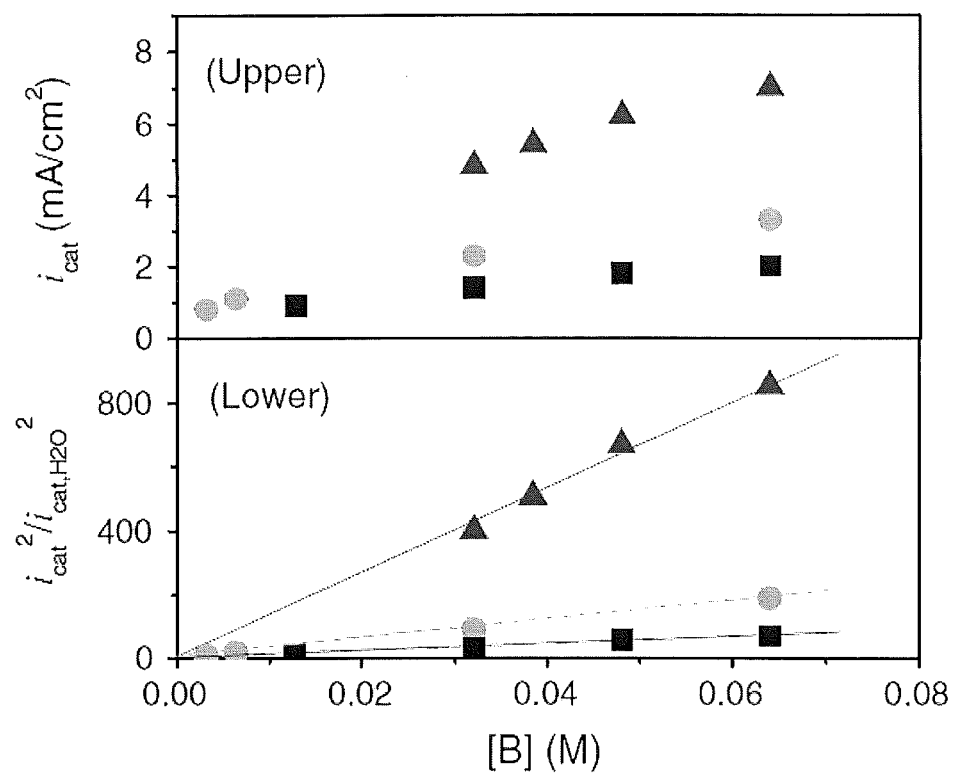
FIG. 22 describes the variations in catalytic current density. The upper graph shows the variations in catalytic current density. ($i_{cat}$ in mA/$cm^2$; background subtracted) for 1 mM [Ru(Mebimpy)(bpy)($OH_2$)]$^{2+}$ at a GC electrode at room temperature with added bases: $H_2PO_4^-$ at pH 2.4 (■), $OAc^-$ at pH 5 (●), and $HPO_4^{2-}$ at pH 7.45 (▲). The Lower graph shows the plots of vs. [B]. Ionic strength (I=0.1 M) was maintained with added $KNO_3$; scan rate, 100 mV/s.

The impact of the addition of proton bases such as $H_2PO_4^-$, acetate (OAc$^-$), or HPO$_4^{2-}$ on the catalytic currents (e.g., $i_{cat}$ (the catalytic current in mA/cm$^2$)) for water oxidation catalyzed by [Ru(Mebimpy)(bpy)(OH$_2$)]$^{2+}$ has also been studies. As shown in FIG. 22, the upper, $i_{cat}$ for [Ru(Mebimpy)(bpy)(OH$_2$)]$^{2+}$ increases with increasing base concentration. This is a base effect and not a pH effect. Variations in the HOAc/OAc$^-$ buffer ratio and pH from 4 to 5.75 at fixed [OAc$^-$] (0.064 M) had no effect on $i_{cat}$.

The data in FIG. 22 and the rate constants in Table 3 illustrate that significant rate enhancements occur for the base catalyzed pathways. For example, $i_{cat}$ reaches 9.1 mA/cm$^2$ in a solution 0.1 Min in HPO$_4^{2-}$ (pH 7.45) at 100 mV/s compared to 0.24 mA/cm$^2$ in 0.1 M HNO3. The addition of even higher concentrations of OAc$^-$ or HPO$_4^{2-}$ resulted in no further current enhancements. Evidence for anation is found in a shift in the intense metal-to-ligand charge transfer absorption band for [Ru$^{II}$(Mebimpy)(bpy)(OH$_2$)]$^{2+}$ from 486 nm in 0.01-0.1 M OAc⁻ to 490 nm in 1 M OAc⁻. Catalysis is lost with anation since $Ru^V=O^{3+}$ is no longer accessible by oxidation and proton loss from $Ru^{II}-OH_2^{2+}$.

Figure 23:
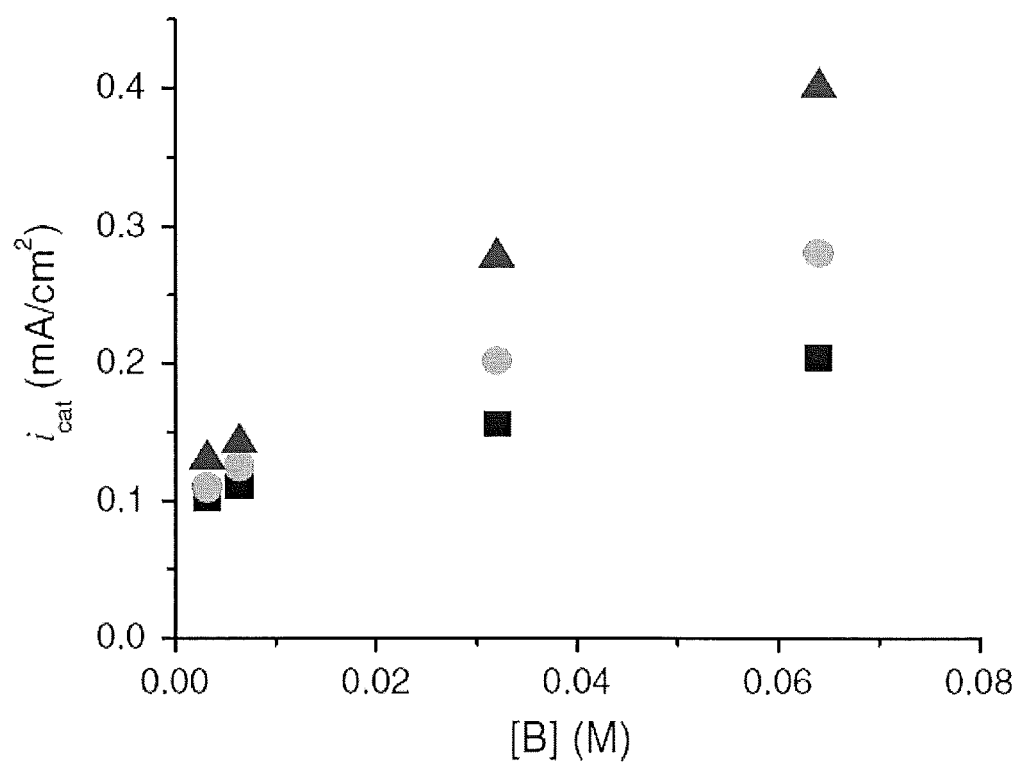
FIG. 23 shows the variations in $i_{cat}$ (background subtracted) at ITO|1-$PO_3H_2$ with added bases, $H_2PO_4^-$ at pH 2.4 (■), $OAc^-$ at pH 5 (●), and $HPO_4^{2-}$ at pH 7.45 (▲). Ionic strength (I=0.1 M) was maintained with added $KNO_3$.

The related phosphonate derivative {Ru(Mebimpy)[4,4'-((HO)$_2$OPCH$_2$)$_2$bpy](OH$_2$)}$^{2+}$ was shown to function as a water oxidation catalyst when surface bound to Sn(IV)-doped In$_2$O$_3$ (ITO) or fluorine doped SnO$_2$ (FTO) electrodes, or in nanoparticle TiO$_2$ films on FTO (FTO|TiO$_2$). Surface binding of the catalyst is important in accelerating rates and in minimizing the amount of catalyst used in an electrocatalytic or photoelectrocatalytic application. As shown by the data in FIG. 23, significant current enhancements with added bases are also observed for 1-PO$_3$H$_2$ on ITO (ITO|1-PO$_3$H$_2$).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A complex having the structure of formula (I):

(I)

wherein M is ruthenium (Ru) or osmium (Os), L$_1$ is a bidentate ligand, L$_2$ is a tridentate ligand, and L$_3$ is OH$_2$, n is 2 or 1.

2. The complex of claim 1, wherein L$_2$ is a tridentate ligand selected from the group consisting of

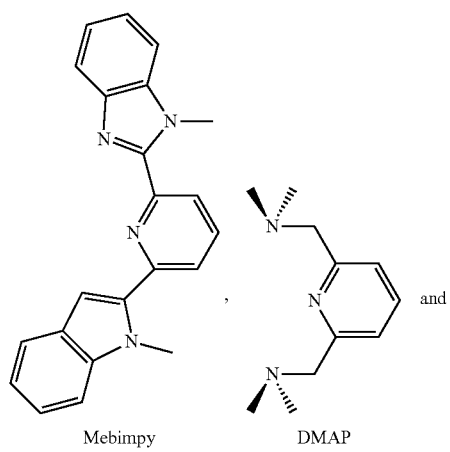

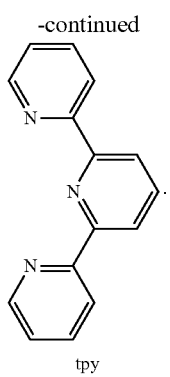

3. A catalyst comprising a complex according to formula (I):

(I)

wherein M is ruthenium (Ru) or osmium (Os), L$_1$ is a bidentate ligand, L$_2$ is a tridentate ligand, and L$_3$ is OH$_2$, n is 2 or 1.

4. A photo-electrochemical cell comprising a catalyst comprising a complex according to formula (I):

[L$_1$—M—L$_2$]$^{n+}$, (I)

wherein M is ruthenium (Ru) or osmium (Os), L$_1$ is a bidentate ligand, L$_2$ is a tridentate ligand, and L$_3$ is OH$_2$, n is 2 or 1.

5. The photo-electrochemical cell of claim 4, wherein, in the complex according to formula (I), L$_1$ is a bidentate ligand selected from the group consisting of

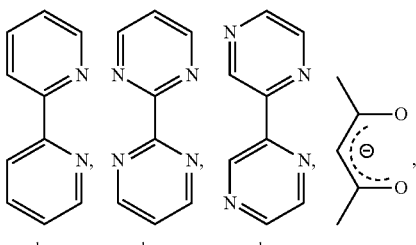

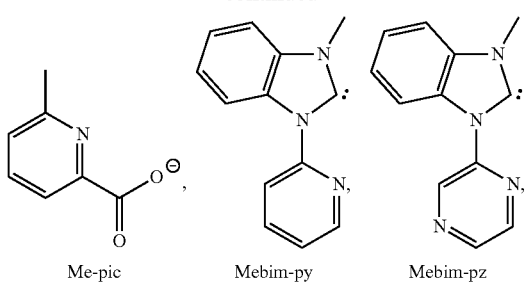

Me-pic, Mebim-py, Mebim-pz

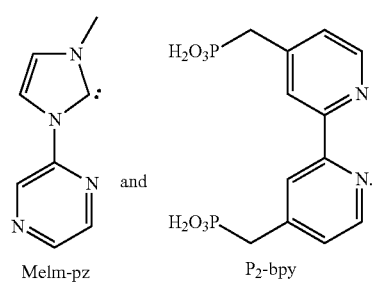

Melm-pz, P₂-bpy

6. The photo-electrochemical cell of claim 4, wherein the complex according to formula (I) comprises the structure {Ru(Mebimpy)[4,4'-((HO)$_2$OPCH$_2$)$_2$bpy](OH$_2$)}$^{2+}$.

7. The photo-electrochemical cell of claim 4, wherein the complex according to formula (I) comprises a complex of Formula A or B:

Formula A

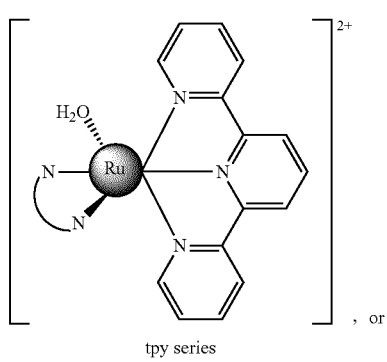

, or tpy series

Formula B

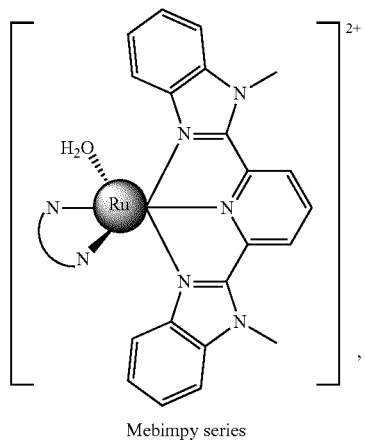

Mebimpy series wherein, for Formula A and B, the ligand

is independently selected from the group consisting of

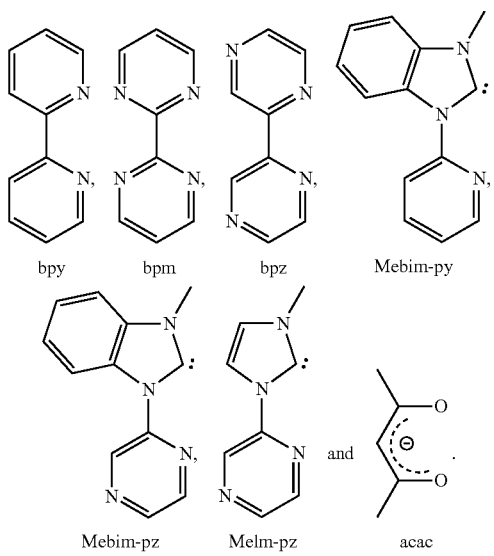

bpy, bpm, bpz, Mebim-py, Mebim-pz, Melm-pz, and acac

* * * * *